US012076449B2

(12) United States Patent
Irizarry et al.

(10) Patent No.: US 12,076,449 B2
(45) Date of Patent: Sep. 3, 2024

(54) DRY FOG PRODUCTION AND APPLICATION METHODS AND SYSTEMS

(71) Applicant: Bio Domain Systems Corporation, Raleigh, NC (US)

(72) Inventors: Harold Irizarry, Indiatlantic, FL (US); Brian Conner, Guntersville, AL (US); Michael Conner, Guntersville, AL (US); Robert Bell, Guntersville, AL (US)

(73) Assignee: Bio Domain Systems Corporation, Raleigh, NC (US)

( * ) Notice: Subject to any disclaimer, the term of this patent is extended or adjusted under 35 U.S.C. 154(b) by 829 days.

(21) Appl. No.: 17/215,824

(22) Filed: Mar. 29, 2021

(65) Prior Publication Data

US 2021/0260227 A1      Aug. 26, 2021

Related U.S. Application Data

(63) Continuation of application No. PCT/US2019/053908, filed on Sep. 30, 2019.

(60) Provisional application No. 62/739,171, filed on Sep. 29, 2018.

(51) Int. Cl.
| A61L 2/00 | (2006.01) |
| A01K 43/00 | (2006.01) |
| A61L 2/26 | (2006.01) |
| A61L 101/06 | (2006.01) |

(52) U.S. Cl.
CPC .............. *A61L 2/0094* (2013.01); *A61L 2/26* (2013.01); *A01K 43/005* (2013.01); *A61L 2101/06* (2020.08); *A61L 2202/122* (2013.01); *A61L 2202/15* (2013.01)

(58) Field of Classification Search
CPC ...... A61L 2/0094; A61L 2/26; A61L 2101/06; A61L 2202/122; A61L 2202/15
See application file for complete search history.

(56) References Cited

U.S. PATENT DOCUMENTS

| 6,391,259 B1 | 5/2002 | Malkin et al. |
| 2007/0065335 A1 | 3/2007 | Bedard et al. |
| 2016/0095949 A1 | 4/2016 | Adams et al. |

FOREIGN PATENT DOCUMENTS

GB          2483552 A    *  3/2012   ............ A61L 2/208

OTHER PUBLICATIONS

ISA/US, International Search Report and Written Opinion for corresponding PCT Patent Application No. PCT/US2019/053908, mailed Dec. 4, 2019, 5 pages.
WIPO, International Preliminary Report on Patentability for corresponding PCT Patent Application No. PCT/US2019/053908, dated Mar. 23, 2021, 4 pages.

\* cited by examiner

*Primary Examiner* — Sean E Conley
(74) *Attorney, Agent, or Firm* — NK Patent Law

(57) ABSTRACT

A method of treating a biological surface. The method includes a first generator dispersing a first dryfog within a sealed chamber, then exhausting the first dry fog from the sealed chamber. Further the first generator or a second generator dispersing a second dry fog within the sealed chamber, then exhausting the second dry fog from the sealed chamber.

14 Claims, 16 Drawing Sheets

DRY FOG PRODUCTION AND APPLICATION METHODS AND SYSTEMS

CROSS-REFERENCE TO RELATED APPLICATIONS

This application is a continuation of PCT Patent Application No. PCT/US2019/053908 filed on Sep. 30, 2019, which claims priority to U.S. Provisional Patent Application No. 62/739,171 filed on Sep. 29, 2018, the entire contents of all of which are incorporated by reference herein.

TECHNICAL FIELD

This disclosure is related to methods and systems for use with dry fog dispersant production, preservation, delivery and collection. The methods and systems described herein may be used to clean, sanitize and preserve of surfaces, spaces, objects and biological materials using one or more controlled dry fog dispersants.

BACKGROUND

Dry fog delivery systems may be used to sanitize or disinfect the air and surfaces in an enclosed space in a manner that doesn't moisten surfaces exposed to the particles. The delivery technologies of the prior art may range from specialized spray nozzles that emit a broad spectrum of particle sizes (see, e.g., U.S. Pat. No. 6,161,778 by James Haruch, which is herein incorporated by reference in its entirety) to vibrating mesh systems that produce uniformly sized particles (see, e.g., U.S. Pat. No. 8,555,874 to Fink, et al. and U.S. Pat. No. 10,335,558 to Boucher, et al., both of which are herein incorporated by reference in their entirety).

In recent years, the poultry industry has struggled to identify and implement effective biosecurity procedures. The removal of antibiotics from the poultry production process and the prevalence and pervasiveness of antibiotic resistant pathogenic microbes has resulted in fewer birds hatching. A large percentage of the birds that do hatch may be infected with a pathogen, and an evenlarger percentage of birds may be contracting illnesses from sick birds within their flock. One way to prevent the transmission of pathogens that originate at the breeder farm to a hatching egg or hatched chick is to enhance the protective cuticle that the hen naturally applies to the eggshell during its final stages of development.

Egg fumigation systems of the prior art may evaporate or atomize a biocide for reducing the microbial load on the eggshell surface, but the biocide fails to prevent the recontamination of the eggshell surface. Disclosed herein is an artificial egg cuticle application system applied through a dry fog delivery system.

Dry fog particles may be small enough to keep the egg surface dry, but large enough toprevent their penetration into the egg through the eggshell pores (see, e.g., La Scala Jr, N, Boleli, IC, Ribeiro, LT, Freitas, D, & Macari, M. (2000). Distribuição do Tamanho de Porns em Cascas de Ovos Determinada pela Porosimetria de Mercúrio. Brazilian Journal of Poultry Science, 2(2), 177-181, hereinafter "Scala, et al.", which is incorporated herein by reference in its entirety). The dry fog may be composed of dissolved physical protective agents, cleaning agents, antimicrobial agents and/or chemical reagents that precipitate antimicrobial deposits onto the eggshell. Unlike biocide applications, which may become less effective as evaporation occurs, the antimicrobial deposits created by the dry fog artificial cuticle disclosed herein remain on the eggshell surface even after the water component in each particle has evaporated. Such an application enables the artificial cuticle's physical defense and biostatic action to persist throughout the egg storage, incubation and hatching period.

Further, the artificial cuticle disclosed herein supplements the often blotchy natural cuticle. The natural cuticle, specifically one applied to an egg by an older hen, leaves many of the eggshell pores uncovered and hence the embryo more exposed to pathogenic microbes. The artificial cuticle is evenly applied, creating a physical layer of protection to the entire surface of the eggshell that minimizes the ability of pathogens to enter the egg through the pores.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

According to at least one embodiment, a system for creating and dispersing a dry fog is disclosed, the system comprising a production system for producing hypochlorous acid and a preservation system for preserving hypochlorous acid and a dry fog system for creating dry fog droplets of hypochlorous acid.

According to at least one embodiment, a method of treating a biological surface, comprising: a first generator dispersing a first dry fog within a sealed chamber; exhausting the first dryfog from the sealed chamber; the first generator or a second generator dispersing a second dry fog within the sealed chamber; exhausting the second dry fog from the sealed chamber.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

FIG. 1 is a schematic view of the production system according to one or more embodiments of the present invention.

FIG. 2 is a schematic view of the preservation system according to one or more embodiments of the present invention.

FIG. 3 is a flow diagram of the control unit maintaining a condition according to one or more embodiments of the present invention.

FIG. 4 is a schematic view of the dry fog delivery system according to one or more embodiments of the present invention.

FIG. 5 is a schematic view of the dry fog delivery system according to one or more embodiments of the present invention.

FIG. 6 is a flow diagram of the control unit operating the dry fog delivery system according to one or more embodiments of the present invention.

FIG. 7 is a free chlorine pH dissociation curve.

FIG. 8 is a schematic view of the collection system according to one or more embodiments of the present invention.

FIG. 9 is a schematic view of the particle collection system according to one or more embodiments of the present invention.

DETAILED DESCRIPTION

Figure 1:
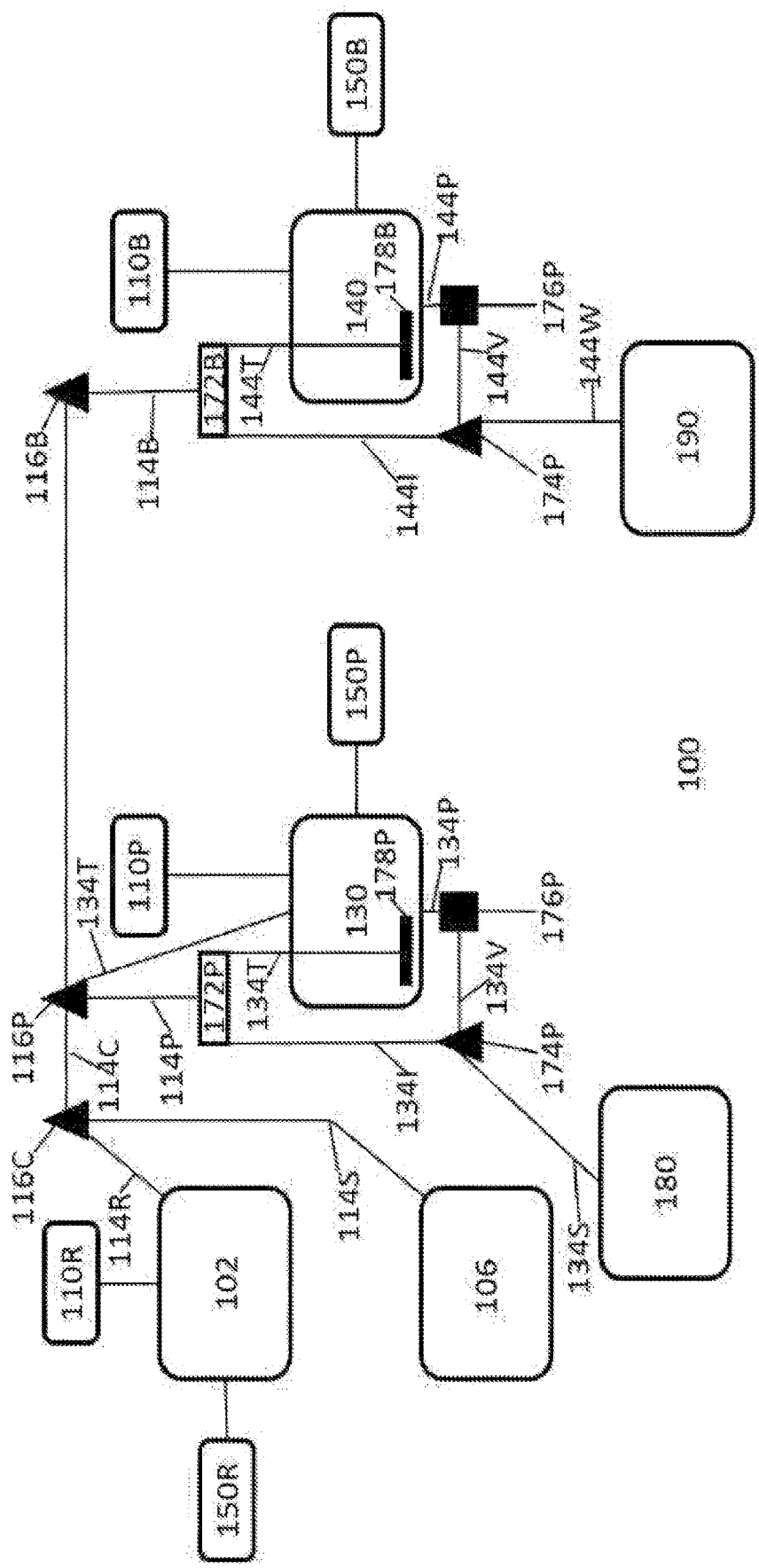

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies.

These descriptions may be presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions may be provided for exemplary purposes. Thus, not all embodiments within the scope of the drawings and these descriptions may be made according to such exemplary dimensions. The drawings may be not made necessarily to scale. Thus, not all embodiments within the scope of the drawings and these descriptions may be made according to the apparent scale of the drawings with regard to relative dimensions in the drawings. However, for each drawing, at least one embodiment is made according to the apparent relative scale of the drawing.

Although the present disclosure is directed towards chicken eggs for ease of discussion and understanding, the methods and systems described herein may be applicable to a number of biological surfaces, non-biological surfaces or other spaces or objects without further undue experimentation. Further, artificial cuticles may be found amongst numerous fowl species, including, but not limited to: chicken, turkey, partridge, quail, pheasant, grouse, guiney, peacock, duck, goose, megapode, and chukar.

Solution Production System.

The production system 100 described herein may be used to create any numbers of solutions 10, including but not limited to the solutions 10 disclosed herein. Solutions 10 may also be acquired or produced using other methods described herein, including using solutions 10 created by the production system 100. In some embodiments, one or more cleaning solutions 10A, one or more artificial cuticle solutions 10B, and/or one or more treatment solutions 10C may be created and utilized by the dry fogging system 1.

Production of one or more solutions 10 may involve mixing one or more agents 14 and one or more production reagents 12P.

According to one embodiment of the invention, and as depicted in FIG. 1, the solution production system 100 may include one or more reaction tanks 102 and/or storage tanks 106 for housing and delivering the one or more agents 14 to a production tank 130 for creating a solution 10. In some embodiments including a reaction tank 102, excess or unwanted agents 14 may be delivered to a neutralizing tank 140 for elimination or conversion of the agents 14 to an innocuous neutralized byproduct 22. The solution 10 may be delivered from the production tank 130 via a production solution hose 134S to a solution tank 180 for transport, to a preservation system 200 for preservation, and/or to a fog tank 310, reservoir 374, reservoir tank 380 or generator 320 for generation of dry fog droplets 302. The neutralizing byproduct 22 may be delivered from the neutralizing tank 140 via a neutralizing waste hose 144W to a waste tank 190 for disposal.

In various embodiments of the solution production system 100, the production tank 130 may include reagent production apertures 132R engageable, or in sealed engagement, with production reagent delivery system(s) 110P for delivering production reagents 12P to the production tank 130.

In addition to the production reagent delivery systems 110P, the production tank 130 may be sealingly engaged with a production injection system 170P for delivering and incorporating the agents 14 into the production tank 130. The injection system 170P may include a production injector 172P, a production flow valve 174P, a production pump 176P, and/or a plurality of production hoses 134.

This mixture of agents 14 and production reagents 12P may continue until the production tank 130 and/or solution 10 fall within certain conditions 2. Sensors 160 inserted into and/or housed within the production tank 130 and/or production injection system 170P may sense actual conditions 22 for permitting determination of whether the conditions 2 have been reached. For example, the conditions 2 may include a range for pH, pressure, temperature, humidity, gas presence/concentration, particle counts and/or chemical molarities or concentrations. Sensors, such as apH sensor 160P, temperature sensor 160T and/or concentration sensor 160C, sensing the actual conditions 22 may permit manual and/or automatic shut off or turn on of any number of valves 116, 174, 188. In one embodiment, once the solution 10 is within a certain pH range, the production gas valve 116P may be closed, the production pump 176P may be turned off, and/or the production flow valve 174P may be closed.

In one embodiment, the sensors 160 may be used to sense actual conditions 22 of the production reagents 12P before the agents 14 is introduced to the production tank 130. The conditions 2 of the production reagents 12P may correspond to a target concentration and/or pH of the solution 10.

Once the solution 10 has been produced and/or solution 10 has reached a target concentration, pH or other specified property, the valves 116, 174, 188 and/or pumps 176 may be manipulated to control flow of the agents 14 and/or solution 10 within the system 100. In one embodiment, the production gas valve 116P may be turned off, ceasing flow of the agents 14 to the production tank 130. The production flow valve 174P may be actuated to cease flow of the production solution 10 to the injector production hose 1341. In some embodiments, the production pump 176P may be activated (or remain in activation) and the production flow valve 174P may be actuated to enable fluid communication with a release production hose 134R for withdrawing the solution 10 from the production tank 130 and into a solution tank 180 for storing the solution 10.

A production cleaning system 150P may be engaged with a production cleaning aperture 132C of the production tank 130. As described herein, a cleaning system 150 generally may deliver cleaning solution(s) 152, such as a production cleaning solution 152P, for neutralizing, removing and/or cleaning a tank 102, 106, 130, 140.

EXAMPLE 2. In one embodiment of the invention, the method of producing a solution 10 being hypochlorous acid (HOCl) using the production system 100 includes the production injector receiving a gas 14 being chlorine gas (Cl2) and the production tank 130 receiving sodium hydroxide (NaOH) and water (H2O) production reagents 12P (or receiving a sodium hydroxide solution as a reagent 12P). In such an embodiment, the sodium hydroxide solution (NaOH+H2O) will continually mix with the chlorine gas (Cl2) by the cycling through the production injection system 170, creating the solution 10 hypochlorous acid (HOCl), as well as production byproducts 16P intermediate hydrochloric acid (HCl), an intermediate byproduct, and salt (NaCl) and water, final byproducts (NaOH+Cl2+H2O→NaOH+ HOCl+HCl→NaCl+H2O+HOCl), as the sodium hydroxide (NaOH) continues to react with the chlorine gas (Cl2) and the hydrochloric acid (HCl).

Introducing, for example, a sodium hydroxide solution with a pH of 12.59 (as sensed bya pH sensor 160P positioned within the production delivery system 110P and/or production tank 130) produces a hypochlorous acid (HOCl) concentration of 2200 ppm at 6 pH (as sensed by a pH sensor 160P within the production injection system 170P and/or production tank 130). Referring to the free chlorine pH dissociation curve, the mixture of chlorine gas (Cl2) and the sodium hydroxide solution with a pH of 12.59 will initially create OCl—, and Na+, and as the NaOH is reduced and the OH is neutralized, the Na+ becomes more attracted to the H, the HOCl concentration increases as the pH lowers.

Upon production of the desired amount or quantity of hypochlorous acid, any excess sodium hypochlorite in the production tank 130 may be neutralized by the addition of sodium thiosulfate (or additionally a sodium hydroxide solution) from the production cleaning system 150P to the production tank 130 (Na2S2O3+4NaOCl+ 2NaOH→2Na2SO4+H2O+4NaCl), thereby halting the production of chlorine gas, leaving only salt (NaCl) and sodium sulfates (Na2SO4), which are both highly soluble in water. Water may be added by the cleaning system 150P until the production tank 130 is flushed and specified cleaning conditions 2 with the production tank 130 are reached.

Solution Production System—Neutralizing Tank.

Any excess solution 10, reagents 12, agents 14, byproducts 16 and/or cleaning solutions 152 in the reaction tank 102, storage tank 106, production tank 130, reagent delivery systems 110, gas delivery systems 112, cleaning systems 150 and/or injection systems 170 may be transported to one or more neutralizing tanks 140. Neutralizing tanks 140 may be useful for neutralizing any solution 10, reagents 12, agents 14, byproducts 16 and/or cleaning solutions 152 that may be considered harmful or undesirable. Transportation to the neutralizing tank 140 may be effectuated using any number of hoses 114, 134, 144, pumps 176 and/or valves 116, 174, 188 of the system 100. In some embodiments additional hoses 184, additional pumps 186 and additional valves 188 may be configured for permitting direct transport from reaction tank 102, storage tank 106, production tank 130, reagent delivery systems 110, gas delivery systems 112, cleaning systems 150 and/or injection systems 170 to the neutralizing tank 150 using the methods and systems described herein and/or disclosed in the prior art.

Any solution 10, reagents 12, gas 14, byproducts 16 and/or cleaning solutions 152 received into, or subsequently produced within, the neutralizing tank 140 may be labeled a neutralizing mixture 20B.

In reagent or combination systems 100R, 100C, the neutralizing tank 140 may include reagent neutralizing apertures 142B engageable, or in sealed engagement, with neutralizing reagent delivery system(s) 110B for delivering neutralizing reagents 12B to the neutralizing tank 130.

In addition to the neutralizing reagent delivery systems 110B, the neutralizing tank 140 may be sealingly engaged with one or more neutralizing injection systems 170B for delivering and incorporating the gas 14 (or neutralizing mixture 20B) into each the neutralizing tank 140. Each injection system 170B may include a neutralizing injector 172B, a neutralizing flow valve 174B, a neutralizing pump 176B, and/or a plurality of neutralizing hoses 144.

The neutralizing pump 176B may be sealingly engaged with the neutralizing tank 140 via a pump hose 144P for initially drawing out and accepting the neutralizing reagent (s) 12B previously and/or concurrently received by the neutralizing tank 140 through the neutralizing reagent delivery system 110B. The neutralizing pump hose 144P may be sealingly engaged with a neutralizing pump aperture 142P which may be positioned on a nadir, a lower side/surface or a lower quarter of the neutralizing tank 140 (such a position allowing for reagent(s) 12B which have collected in the lower portion of the neutralizing tank 140 to be retrieved). The reagent(s) 12B drawn out by the pump hose 144P may be delivered through the pump 176B and towards the flow valve 174B through a neutralizing flow hose 144F sealingly engaged with both the pump 176B and the flow valve 174B.

This mixture of neutralizing mixture 20B and production reagents 12B may continue until the actual conditions 22 within the neutralizing tank 140 and/or the neutralizing byproducts 16B fall within the conditions 2. Sensors 160 inserted into and/or housed within the neutralizing tank 140 and/or neutralizing injection system 170B may sense the actual conditions 22 for permitting determination of whether the conditions 2 of the neutralizing mixture 20B have been reached. For example, the conditions 2 may include a range for pH, pressure, temperature and/or chemical molarities or concentrations. Sensors, such as a pH sensor 160P, temperature sensor 160T and/or concentration sensor 160C, sensing the actual conditions 22 may permit manual and/or automatic shut off or turn on of any number of valves 116, 174, 188. In one embodiment, once the neutralizing mixture 20B is within a certain pH range, the neutralizing gas valve 116B may be closed, the neutralizing pump 176B may be turned off, and/or the neutralizing flow valve 174B may be closed.

In one embodiment, the sensors 160 may be used to sense actual conditions 22 of the neutralizing reagent(s) 12B before the gas 14 or neutralizing mixture 20B is introduced to the neutralizing tank 140. The conditions 2 of the neutralizing reagent(s) 12B may correspond to a target concentration and/or pH of the neutralizing mixture 20B.

Once the neutralizing mixture 20B and/or solution 10 has reached a target concentration, pH or other specified property, the valves 116, 174, 188 and/or pumps 176 may be manipulated to control flow of gas 14, mixture 20 and/or solution 10 within the system 100. In one embodiment, the neutralizing gas valve 116B or additional valve 188 may be turned off, ceasing flow of gas 14 or the neutralizing mixture 20B to the neutralizing tank 140. The neutralizing flow valve 174B may be actuated to cease flow of the neutralizing mixture 20B to the injector neutralizing hose 144I. In some embodiments, the neutralizing pump 176B may be activated (or remain in activation) and the neutralizing flow valve 174B may be actuated to enable fluid communication with a release neutralizing hose 144R for withdrawing the mixture 20B from the neutralizing tank 140 and into a waste tank 190 for storing the mixture 20B.

A neutralizing cleaning system 150BP may be engaged with a neutralizing cleaning aperture 142C of the neutralizing tank 140. As described herein, a cleaning system 150 generally maydeliver cleaning solution(s) 152, such as a neutralizing cleaning solution 152B, for neutralizing, removing and/or cleaning a tank 102, 106, 130, 140, 180, 190.

Any hypochlorous acid and/or sodium hypochlorite in the neutralizing tank 140 may be diverted to the waste into a waste tank 190 or remain in the neutralizing tank 140 for neutralization with neutralizing reagents 12B water, sodium thiosulfate and sodium hydroxide. These neutralizing reagents 12B may be combined with HOCl and undergo multiple reactions with free and combined chlorine, depending on the solution pH. The amount of sodium thiosulfate desired for neutralization will vary with the solution pH sensed. Any hydrochloric acid produced may be salted out by the sodium hydroxide (HCl+NaOH→NaCl+H2O).

In a further embodiment, the hypochlorous acid stored in the waste tank 190 or the neutralizing tank 140 may be mixed with sodium thiosulfate and sodium hydroxide solution, after which the waste tank 190 or neutralizing tank 140 may be sealed and shaken for a duration (e.g., 10-30 seconds, 20 seconds or some other range).

Preservation of Solutions.

Figure 2:
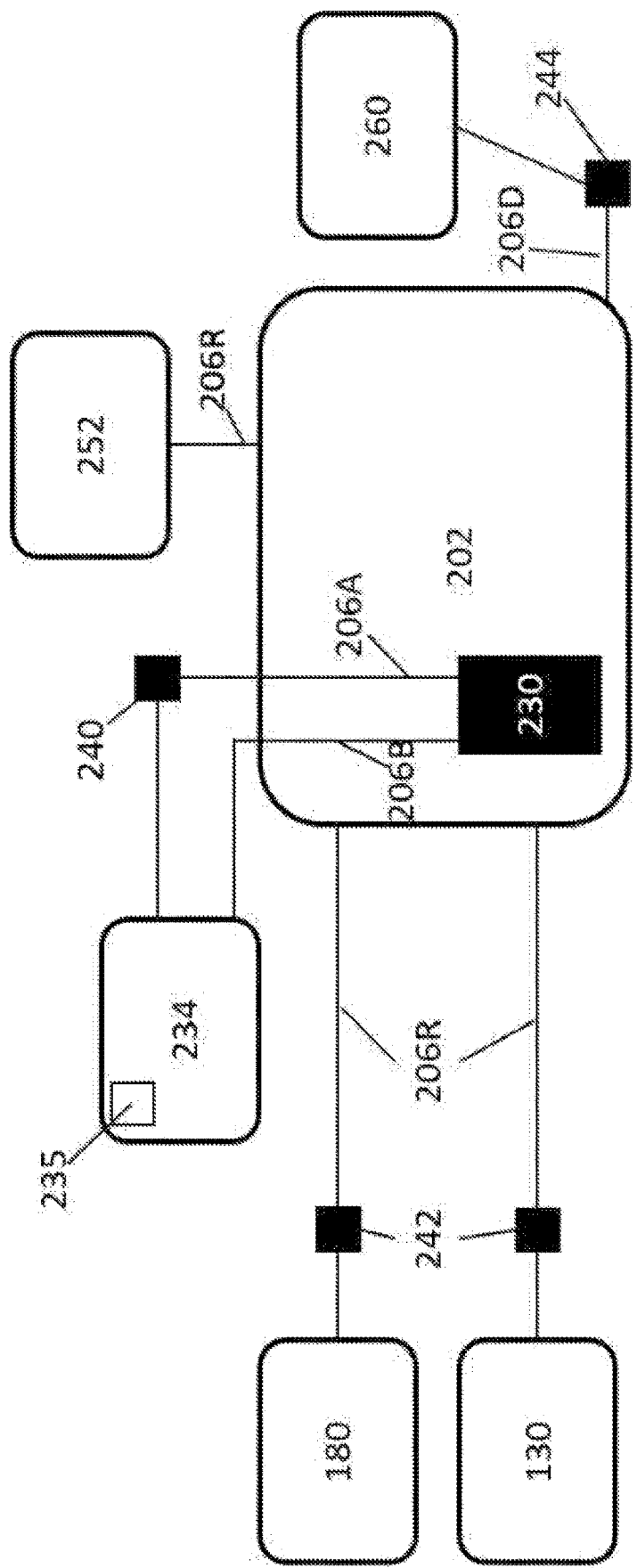

According to further embodiments of the disclosed system 1, once a solution 10 is produced by the production system 100, or acquired or stored via other means, a preservation system 200 and methods of use may preserve the solution 10. As is depicted in FIG. 2, the preservation system 200 may include a preservation tank 202 for storing and preserving the solution 10. In some embodiments of the system 1, the preservation tank 202 of the preservation system 200 is the same solution tank 180 of the production system 100 and may be engaged to both systems 100, 200 and incorporated for use in each system 100, 200 accordingly. In other embodiments, the solution tank 180 may be disengaged and sealed from the production system 100 for transportation and engagement with the preservation system 200 for use as a preservation tank 202 therein. In other embodiments, the solution tank 180 and/or another solution tank 181 may be in engageable with the preservation tank 202.

The preservation tank 202 may include an reception preservation aperture 204R for receiving the solution 10 from a reception preservation hose 206R in sealed and fluidic engagement with a solution tank 180, another solution tank 181 and/or another receptacle housing the solution 10. Due to instability of many solutions 10, the tanks 180, 181, 202, as is more fully described above, may be configured, amended and/or manufactured for blocking ultraviolet light or sunshine, minimizing contact with environmental air, controlling the temperature and/or minimizing adverse interactions with the tank 180, 181, 202 components and/or surfaces.

To measure when the solution 10 is within a temperature range, the preservation system 200 and/or preservation tank 202 may include a temperature sensor 160T for sensing a temperature of the solution 10 and/or within the preservation system 200 or tank 202. The temperature sensor 160T may be positioned within or on the preservation system 200 and/or preservation tank 202 or may insertable therewithin.

To measure when the solution 10 is within a pH range, the preservation system 200 and/or preservation tank 202 may include a pH sensor 160P for sensing a pH of the solution 10 and/or within the preservation system 200 or tank 202. The pH sensor 160P may be positioned within or on the preservation system 200 and/or preservation tank 202 or may insertable therewithin.

To measure when the solution 10 is within another property or condition range, the preservation system 200 and/or preservation tank 202 may include one or more other sensors 160 forsensing a property or condition of the solution 10 and/or within the preservation system 200 or tank 202. The one or more sensors 160 may be positioned within or on the preservation system 200 and/orpreservation tank 202 or may insertable therewithin. For example, gas sensors 160G may be included proximal to, and outside of, the preservation tank 202 for measuring the concentration of gas 14 in the environment about the tank 202. One or more of the sensors 160 may be housed together. Additional sensors 160 and their uses are described further herein and may be applied to the preservation system 200.

The preservation system 200 may further include an immersion coil 230 housed within, or insertable within, the preservation tank 202. The immersion coil 230 may define an entry 230A for receiving immersion fluid 232 and an exit 230B from which the immersion fluid 232 may be withdrawn. The preservation system 200 may further include am immersion tank 234 for housing a portion of the immersion fluid 232. The immersion tank 234 may include a refrigeration unit 235 for controlling and maintaining an immersion temperature or range of the immersion fluid 232 within the immersion tank 234. The immersion coil 232 may be made of titanium or stainless steel or another non-reactive material. The chilling fluid 238 may be a concentrated sodium hydroxide (NaOH) solution.

An immersion entry hose 206A may be sealingly engaged with both an immersion exit aperture 238A of the immersion tank 234 and the coil entry 230A for enabling fluidic communication therebetween, the immersion entry hose 206A flowing through, and in sealed engagement with, an entry aperture 204A of the preservation tank 202. An immersion exit hose 206B may be sealingly engaged both with an immersion entry aperture 238B of the immersion tank 234 and the coil exit 230B for enabling fluidic communication therebetween, the immersion exit hose 206B flowing through, and in sealed engagement with, an exit aperture 204B of the preservation tank 202. The cycling of the immersion fluid 232, and the fluidic rate of the cycling, through the immersion tank 234, immersion coil 230 and hoses 206A, 206B may be effectuated by an immersion pump 240 positioned along one of the hoses 206A, 206B.

Though the solution 10 is stored within the preservation tank 202, and certain adverse conditions are avoided, such as exposure to light, ambient air, extreme pH levels and undesired temperatures, the solution 10 may still be predisposed to decomposition over time. To counteract or minimize the decomposition of the solution 10, the preservation tank 202 may include a preservation reagent aperture 204P for engagement with a preservation reagent hose 206P for delivering a preservation reagent 250 to the preservation tank 202. The reagent hose 206P may be in sealed engagement with a preservation reagent tank 252 and/or the immersion tank 234. In embodiments where the immersion fluid 232 may also serve the function of a preservation reagent 250, the immersion tank 234 may define a delivery aperture 238C for engaging the reagent hose 206P. A delivery pump and/or valve 242 may be included along the reagent hose 206P for managing the titration or flow rate of the reagent 250 from the preservation reagent tank 252 and/or immersion tank 234.

In some embodiments, the preservation tank 202 may also define a dispensing aperture 204D through which a dispensing hose 206D may pass in sealed engagement thereto. One end of the dispensing hose 206D may be positioned on a nadir, a lower side/surface or a lower quarter of the preservation tank 202 (such a position allowing for solution 10 which as collected in the lower portion of the preservation tank 202 to be retrieved). A dispensing pump 244 may be engaged with dispensing hose 206D for managing and controlling the fluid flow of the solution 10 from the preservation tank 202. The dispensing hose 206D may be sealably engaged with a preserved solution tank 260 for storing and/or transporting the solution 10.

The various sensors 160, various pumps 240, 242, 244 and/or the refrigeration unit 235 may be in electronic communication with a preservation control unit 220. In other embodiments, the various sensors 160, various pumps 240, 242, 244 and/or the refrigeration unit 235 may be manually operated. In yet other embodiments, some of these components may be manually operated and others may be automatically and/or electronically operated. The preservation control unit 220 may include a number of sub-control units in electronic communication, a display panel, operational controls and/or wireless communication features for operation, as described herein.

In one embodiment of the preservation system 200, a method of maintaining a preservation condition 270 for the solution 10, preservation system 200 and/or preservation tank 202 is provided. The preservation condition 270 may include a value or a specific range of values for one or more specific conditions (e.g., temperature, pH, humidity, time, concentration, etc.). One or more of the sensors 160 may be employed to measure various conditions 2 of the system 1, environment 3, solution 10, preservation system 200 and/or preservation tank 202. An actual preservation condition 272 may be directly measured or may be calculated or determined by the control unit 220 using one or more of the other conditions 2. If the actual preservation condition 272 matches, or falls within, the preservation condition 270, the preservation system 200 may remain unchanged for a waiting period 822P. If the actual preservation condition 272 does not match, or falls without, the preservation condition 270, one or more components of the preservation system 200 may be changed through an action 4.

Figure 3:
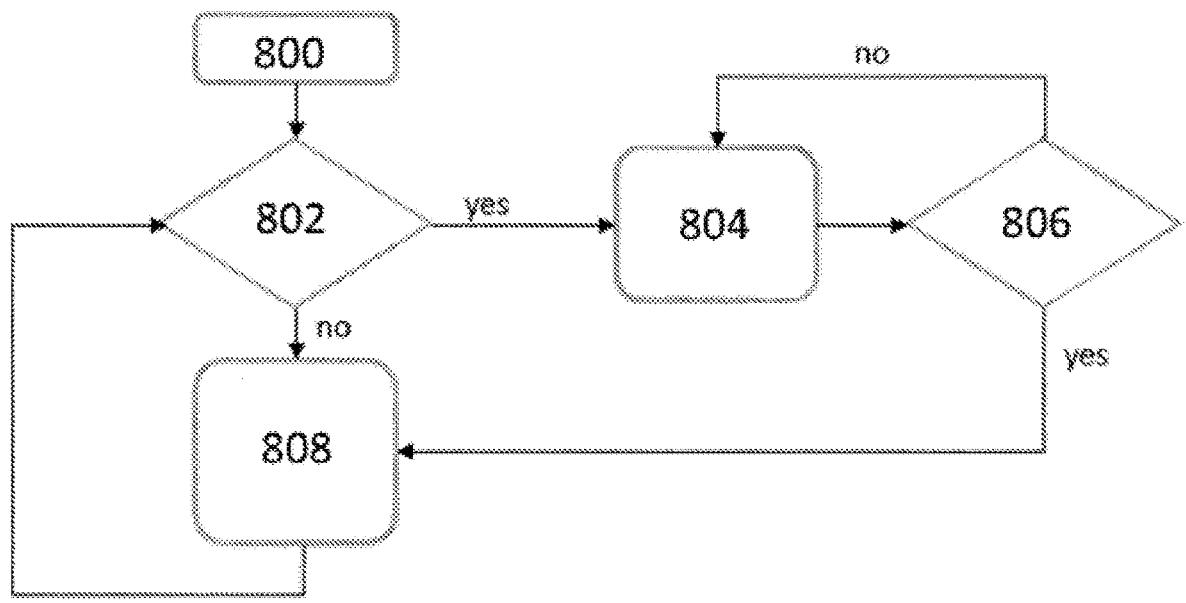

In the embodiment of FIG. 3, the system 1 may start 800, determine if the pH is less than 5.95 802. If yes, then add NaOH solution 804, then determine if the pH is greater than 6.05 806. If yes, then wait for a specified period of time 808.

For example, if the preservation condition 270 is a pH range for the solution 10 and the actual condition 272 is outside the pH range, the delivery pump 242 may be activated for delivering a quantity of preservation reagent 250 to the preservation tank 202 in an attempt to bring the measured pH of the solution 10 within range. Following the action 4 being the pump activation, a waiting period 822P may pass before the actual condition 272 is measured or determined again. If the actual condition 272 is outside the pH range again, the delivery pump 242 may be activated again (i.e., another action 4 is taken) and a waiting period 822P may again pass. If the actual condition 272 then falls within the preservation condition 270 being the pH range, the action 4 may not be taken, and the waiting period 822P again may pass. These methods steps may be performed for any length of time to ensure that the preservation condition 270 is maintained so that the decomposition of the solution 10 is minimized.

The same method steps may be used for any number of preservation conditions 270. In another example, the preservation condition 270 may be a temperature range for the preservation tank 202 and the action may be to activate the immersion pump 240 for cycling immersion fluid 232 through the immersion coil 230 housed within the solution 10. The action 4 may be predefined and may correspond to the actual preservation condition 272 so that the action 4 taken is relative to the difference between the actual condition 272 and the preservation condition 270.

Dry Fog Delivery System.

According to further embodiments of the disclosed system 1, a solution 10 produced by the production system 100 and/or preserved by the preservation system 200 may be dispersed by a dryfog delivery system 300 within an environment 3. The solution 10 may be delivered to the dry fog delivery system 300 from a solution tank 180 for transport, a preservation system 200 for preservation, and/or to a fog tank 310, fog reservoir 374 or fog reservoir tank 380 within the fog system 300 for generation of dry fog droplets 302. Delivery of the solution 10 may be effectuated via any number of hoses, valves, pumps or other mechanisms disclosed herein.

In some embodiments, the environment 3 is closed. The dry fog delivery system 300 may produce droplets 302 of the solution 10 within certain size ranges 304 for dispersal within the environment 3. In some embodiments the size ranges 304 of the droplets 302 produced are under ten microns, between four and ten microns, or under fifteen microns. Dry fog delivery systems 300 disclosed herein may be used to sanitize or disinfect the surfaces 5 or air within an environment 3 in a manner that doesn't moisten the surfaces 5 exposed to the droplets 302.

Solutions

In some embodiments, the solution (or solutions) 10 being delivered to, or utilized by, the fog delivery system 300 includes one or more cleaning solutions 10A, one or more artificial cuticle solutions 10B, and/or one or more treatment solutions 10C. The various solutions 10A, 10B, 10C may each include different components and/or component ratios, and may be reactive or incompatible when stored with each other.

In some embodiments, the surface 5 of the environment 3 is an eggshell. Bumpy and grainy in texture, an eggshell may include tens of thousands of tiny pores. Eggshell is made almost entirely of calcium carbonate ($CaCO_3$) crystals. It is a semipermeable membrane, which means that air and moisture can pass through its pores. The cuticle of an egg, also known as the bloom, is the natural coating or covering on the eggshell that seals the eggshell pores. The cuticle helps to prevent bacteria from getting inside the shell and reduces moisture loss from the egg. In nature, the cuticle dries and flakes off. When an egg is newly laid, it is about 105° F. (41° C.) and has either no air cell or a very smallone. As the egg cools, the liquid contents contract more than the shell and the inner shell membrane separates from the outer shell membrane to form the air cell. As the egg ages, moisture and carbon dioxide leave through the pores of the shell, air enters to replace them and the air cell becomes larger.

The pore size distribution in chicken eggs, for example, have been experimentally determined to have 68% of the sample pore diameters between 1.4 and 5.6 micrometers. Dry fog droplets 302 greater than 5.6 micrometers may be small enough to keep the egg surface dry, but large enough to prevent their penetration into the egg through the eggshell pores (see, e.g., La Scala Jr, N, Boleli, IC, Ribeiro, LT, Freitas, D, & Macari, M. (2000). Distribuição do Tamanho de Porns em Cascas de Ovos Determinada pela Porosimetria de Mercúrio. Brazilian Journal of Poultry Science, 2(2), 177-181, hereinafter "Scala, et al.", which is incorporated herein by reference in its entirety).

Hatching eggs may become contaminated when microbes enter the eggshell through thepores or fractures in the eggshell, thereafter multiplying in the yolk sac during incubation. Very few eggs become horizontally contaminated (from the environment or unrelated individuals) prior to being laid. A vertically contaminated egg (acquisition of symbionts from parents, usually mothers) is likely to originate when microbes penetrate the eggshell at oviposition or subsequently through hot to cold temperature changes, the handling of egg, the wetting of egg or by other means. A certain percentage of microbes that enter the yolk sac may produce hydrogen sulfide gas or other gases at levels that cause to egg to explode in the incubator. This explosion spews potentially pathogenic microbes throughout the incubator, increasing the microbial load on the surface of the other incubating eggs. Higher microbial loads on the surface of the eggs during incubation are associated with embryonic death, decreasing hatch percentage, increasing first week mortality percentage, and increasing other indicators of undesirable sanitary conditions. The propagation of pathogenic microbes, especially ones that are anti-biotic resistant, from one poultry farm to another is becoming a major issue at parent stock and broiler farms.

Further, certain countries in Europe have begun to implement regulations mandating the elimination of male chick culling practices at parent stock facilities. Male chicks are not required at several stages during parent stock production. In these instances, the male chicks are culled after hatch. These new regulations leave the parent stock companies with essentially two choices: raise males to maturity or implement a process that may sex the chick prior to hatch.

Of the technologies being considered for embryonic sexing, several of them require that a small incision be made in the egg. This incision will expose the embryo to potentially pathogenic microbes.

It is common practice and, in most cases, a regulatory requirement to vaccinate the chick prior to or after hatch. The in ovo vaccination machines also leave an incision in the egg that exposes the embryo to potentially pathogenic microbes.

The one or more cleanings solutions 10A may include one or more cleaners, antimicrobials and/or disinfectants, such as hypochlorous acid and copper II hydroxide. Copper II hydroxide is known to have antimicrobial properties. According to some embodiments, a copper II hydroxide cleaning solution 10A may be created by applying two distinct dry fogs either simultaneously and/or in an alternating fashion. For example, a sodium hydroxide solution and a copper II chloride solution may be applied, and as the surface 5 of the environment 3 dries, either naturally and/or by applying air circulation, a copper II hydroxide and salt coating remains ($2NaOH+CuCl_2 \rightarrow 2NaCl+Cu(OH)_2$). In some embodiments of the method, the solutions 10A may further include a hypochlorous acid solution, which may be dispersed prior to applying the dry fogging of the copper II hydroxide or two distinct solutions for creating the copper II hydroxide.

The one or more cleaning solutions 10A, once converted to droplets 302 and forming a dry precipitate on an eggshell, for example, may reduce the microbial load or completely disinfect the outer eggshell surface (and the inside of the air cell if exposed). This may allow for higher dosages of the artificial cuticle solution 10B treatment since it reduces or eliminates the risk of contaminating the eggs by wetting them. Even so, the cleaning solution 10A may denature some of the natural eggshell cuticle, and may leave behind harmful fumes or gases which may need to be neutralized.

The one or more artificial cuticle solutions 10B may have sanitary, antiseptic, cleansing, antimicrobial, antifungal, biocidal, bacteriostatic, and/or biostatic properties. The cuticle solutions 10B may provide a physical barrier to a surface 5. The surface 5 may be an eggshell. The cuticle solutions 10B may include one or more proteins and/or enzymes. The cuticle solution may further include copper II hydroxide. The proteins and enzymes may include, but are not limited to, any of the following: Lysozyme, EDTA, Ovotransferrin, Ovocalyxin-32, Cystatin, Ovoinhibitor. The artificial cuticle may also be composed materials with toxin-absorbing properties such as a bioclay. Additionally, the cuticle may also be composed of broad spectrum bacteriophage formulations. The cuticle solution 10B may be deployed to coat eggs with a protective layer that cleans and/or persists throughout the incubation period. Such artificial cuticles may increase hatchability and decrease first week mortality.

The one or more treatment solutions 10C may include bacteriophages and/or probiotics. In some embodiments, the treatment or enhancing solution 10C may include constituents to be absorbed into an egg. When the temperature of an egg is altered from a hotter temperature to a colder temperature, there is a net suction effect into the pores, when may cause the dry fog droplets 302 and/or their constituents, to be absorbed through the pores of the eggshell. The temperature may be monitored or altered to control this effect.

Any of the solutions 10 may incorporate gluten for enabling time release of solution constituents, whereby activation of the gluten with water or humidity permits release of the constituents.

Solutions 10 may include one or more agents 14 or reagents 16. The solutions 10 may be created within the system 1, or delivered thereto in final form. In some embodiments, the agents 14 and/or reagents 16 may be preserved in tanks or delivery systems or receptacles for creating the solutions 10 immediately prior to dispersal by the dry fog system 300. The agents 14 and/or reagents 16 may be in solid, liquid or gas form.

Considering the above disclosure, in some embodiments of the system 1, the resultant dry fog droplets from solutions 10 dispersed by the fog system 300 may be composed of dissolved physical protective, cleaning, antimicrobial and/or chemical agents 14 and/or reagents 16, and/or their byproducts, that precipitate antimicrobial deposits onto the surface 5 of the environment 3. The presently disclosed system 1 offers a solution to the issues of the prior art by applying solutions that may help clean, sanitize, protect and enhance eggshells throughout the incubation process. Further, while the cleaning or sanitizing an eggshell may remove a portion of the natural cuticle thereon, or incisions to the eggshell may be made to inject into the egg, the present system 1 may apply solutions 10B, 10C for protecting and/or enhancing the egg and its newly exposed surfaces. For example, the application of the artificial cuticle solution 10B itself, or in conjunction with other biosecurity practices such as the application of other solutions 10A, 10C, may be integral to the mitigation of contamination problems. Bio-isolation may be achieved by applying the artificial cuticle 10B prior to incubation as well. The sooner an artificial cuticle 10B or other solutions 10 are applied to an egg, the less likely the egg becomes susceptible to vertical contaminated.

Generation of Dry Fog.

Figure 4:
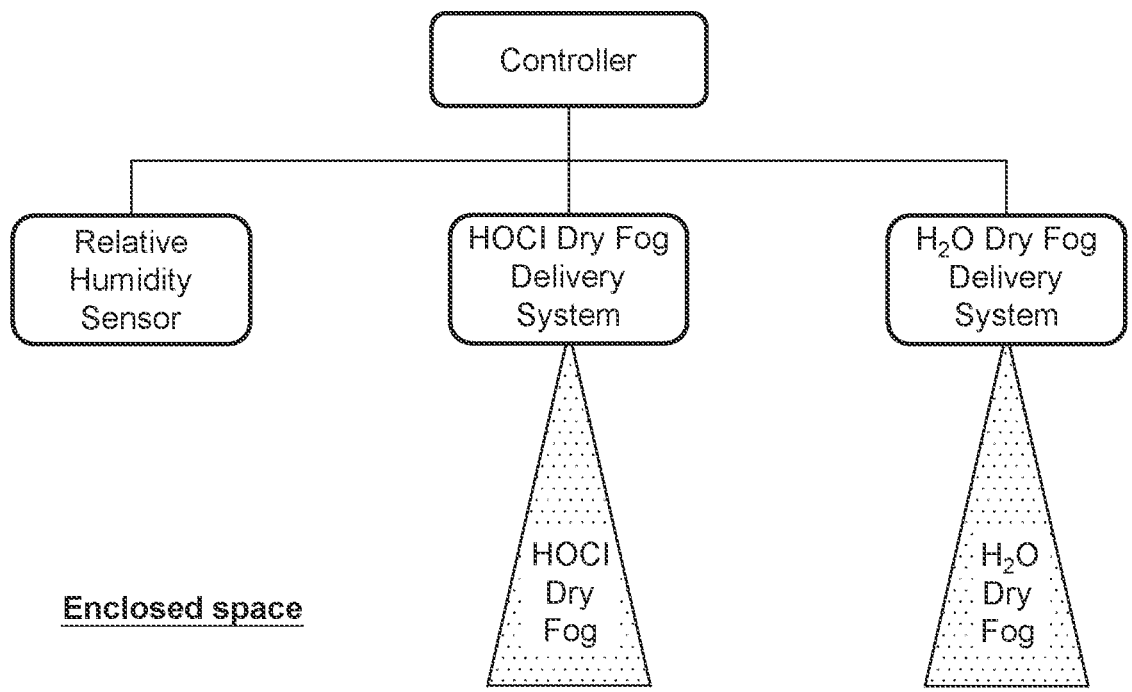
Figure 5:
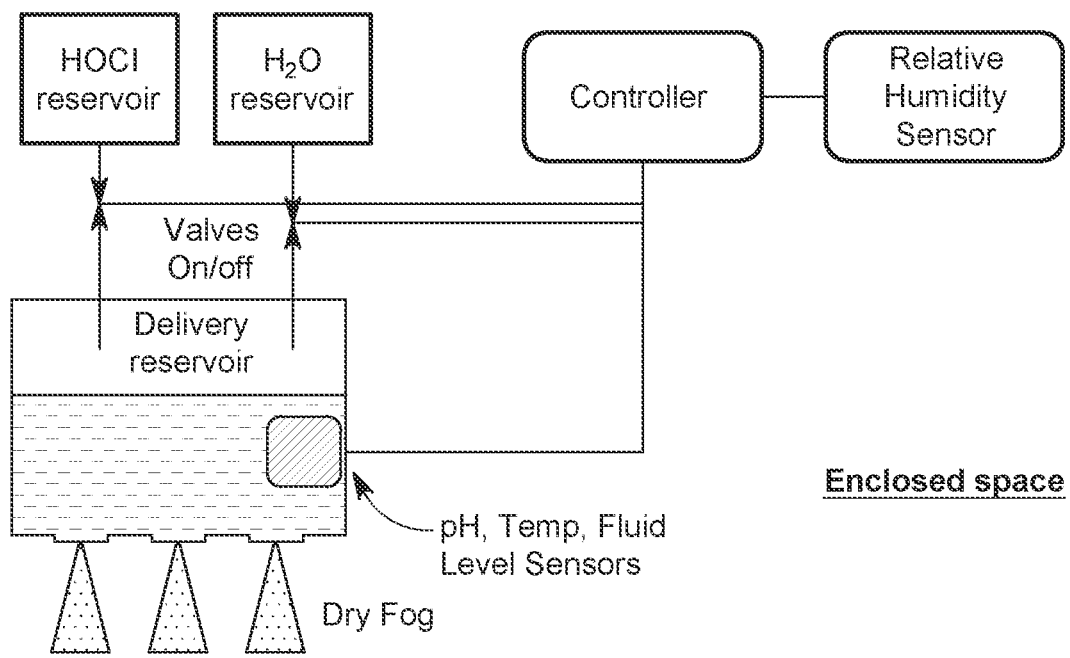

As is depicted in FIGS. 4 and 5, the dry fog delivery system 300 may include one or more fog tanks 310 for housing the solutions 10, or the fog system may be in fluidic communication with one of the other tanks of the system 1 for accepting delivery of solutions 10. In some embodiments of the system 1, the fog tank 310 of the fog delivery system 300 is the same solution tank 180 (or another solution tank 181) of the production system 100, the preservation tank 202 (or preservation solution tank 260) of the preservation system 200 or some other tank of the system 1, and may be engaged one or more of the systems 100, 200, 300 and incorporated for use in one or more of the systems 100, 200, 300 accordingly. In other embodiments, the solution tank 180 (or another solution tank 181) may be disengaged and sealed from the production system 100, or the preservation tank 202 (or preservation solution tank 260) may be disengaged and sealed from the preservation system 200 for transportation and engagement with the fog delivery system 300 for use as a fog tank 310 therein. In other embodiments, the solution tank 180 (or another solution tank 181) or the preservation tank 202 (or preservation solution tank 260) may be in engageable with the fog tank 310.

The fog tank 310 may include a solution reception aperture 312S for receiving the solution 10 from a solution reception hose 314S in sealed and fluidic engagement with a tank of the system I and/or another receptacle housing the solution 10. A fog solution pump 352 may be positioned along the solution reception hose 314S or incorporated into the fog tank 310, other tank of the system 1, and/or another receptacle housing the solution 10 for effectuating the delivery of the solution 10 through the fog tank 310. Due to instability of many solutions 10, the fog tank 310, as is more fully described herein, may be configured, amended and/or manufactured for blocking ultraviolet light or sunshine, minimizing contact with environmental air, controlling the temperature and/or minimizing adverse interactions with the fog tank 310 components and/or surfaces.

The fog tank 310 may further include, or be in fluidic communication with, one or more fog generators 320 for converting the solution 10 into dry fog droplets 302. The fog delivery generator 320 may include one or more nebulizing modules 386 for generating the dry fog. The nebulizing module 386 may be any dry fog droplet generating device known in the prior art. For example, the nebulizing module 386 may be a vibrating mesh nebulizers driven by a piezo disc which pumps the solution 10 through an array of mesh apertures for generating droplets 302. In another example, the nebulizing module 386 may include an ultrasonic transducer, which may be tuned to produce a fine mist of droplets 302. The nebulizing module 386 may take many forms, and may be made from a chemical resistance coating or materials with chemically resistant properties such as stainless steel, titanium polyamide, gold, palladium or other chemical resistant materials, metals or plastics.

One advantage of generating dry fog from multiple, distinct solutions 10, instead of pre-mixing solutions 10 prior to dry fog generation, may be to minimize the formation of precipitate collecting in the generator 320 and/or nebulizing module 386. For example, mixing copper II chloride and sodium hydroxide to form the antimicrobial copper II hydroxide often results in the formation of a precipitate, which may result in failure or intense cleaning procedures. The precipitate may, for example, clog up a generator 320 and/or nebulizing module 386 or restrict various apertures in the delivery system 300. In further examples, some fluids, such as those formed from dissolved proteins and enzymes, may be incompatible and/or may negatively affect the preservation, consistency and/or decomposition of the solution 10 and/or droplets 302 when combined in a single compartment, such as reservoir 374 or tank of the system 1, for an extended period of time. Advantageously, the multiple, separate reservoirs 374 and/or tanks of the system 1 permit multiple differing droplets 302 to be created, either concurrently, in sequence or both for effectively cleaning, forming a cuticle, and/or treating a surface 5 and/or environment 3.

In some embodiments, the fog tank 310, or other tanks or delivery systems of the system 1, may be in fluidic communication with one or more fog generators 320. One or more of the fog generators 320 may be, or include, one or more fog cartridges 370. As is depicted in FIGS. 13-17, the fog cartridge 370 may include a nebulizing portion 382 and an engaging portion 384. The nebulizing portion 382 and the engaging portion 384 may be unitarily constructed or may be coupled together. The nebulizing portion 382 may include one or more nebulizing module 386 on a nebulizing side 383 for nebulizing a solution 10 into droplets 302 of the dry fog. Each nebulizing module 386 may have an open or closed state and be in fluidic communication with a corresponding reservoir 374 and/or tank of the system 1. In some embodiments, the nebulizing portion 382 of a fog cartridge 370 may include two or more reservoirs 374 for separately housing solutions 10. An end of the reservoir 374 opposite the end engaging the nebulizer module 386 may include a reservoir aperture 387 for receiving the solution 10 therethrough, from either the tank of the system 1, such as a reservoir tank 380, or a delivery system, or both.

In some embodiments, a plurality of reservoir tanks 380 corresponding to one or more of the reservoirs 374 may be included in the dry fog delivery system 300 for storing the fluids for delivery to the corresponding reservoirs 374 via hoses, pumps and/or apertures. Sensors 160 may be incorporated within or proximal these reservoirs 374, reservoir tanks 380 and/or connecting components for sensing various conditions (e.g., fluid levels, temperature, pH, etc.). In other embodiments, the reservoir tanks 380 may also incorporate the systems and methods of the preservation system 200 by doubling as preservation tanks 202.

The engaging portion 384 of the cartridge 370 may include one or more electronic connection pins 388 for receiving electrical communications and actuating the nebulizing module 386 between the open and closed state (the open state configured to generate droplets 302 from the solution 10). The generator 320 may also include a fog receptacle 372 defining an engagement portion 390 for nestingly engaging (or coupling) the engaging portion 384 of the cartridge 370. The fog receptacle 372 may include mating terminals 392 for receiving the connection pins 388 when the receptacle 372 and cartridge 370 are nestingly engaged.

In some embodiments, the fog cartridge 370 may be temperature-controlled or stored within a refrigerated portion of the delivery system 300. Alternatively, the fog cartridge 370 may be housed in an external refrigerator and transported to the delivery system 300 for engagement with the fog receptacle prior to use. Refrigeration may reduce degradation of solutions 10, agents 14 and/or reagents 16 over time. Sensory feedback loops, such as those utilized in the preservation system 200, may be utilized to regulate the temperature of the fog cartridge 370.

In some embodiments, a portion of the fog cartridge 370 may be nestingly engaged within the receptacle 372. Upon engagement, an electrical connection may exist between the connection pins 388 and the mating terminals 392. The mating terminals 392 may be in wireless or electronic communication with the master controller 9, the dry fog control unit 360 or other control units described herein. In other embodiments, the master controller 9, the dry fog control unit 360 or other control units described herein are in wireless or electronic communication with the fog cartridge 370 and/or individual reservoirs 374 or nebulizing modules 386. The electrical connection enables electrical stimulation of any piezo elements included in the nebulizing modules 386 and/or actuation of the nebulizing modules 386. The cartridges 370, receptacles 372 and/or reservoirs 374 or nebulizing modules 386 may include reprogrammable non-volatile memory for storing information.

The interaction between the mating terminals 392 and the connection pins 388 may further serve to provide friction and/or a mechanical retention for holding the cartridge 370 in position relative to the receptacle 372. Other friction or mechanical retentions may also be provided, such as a locking ramp and corresponding divot, a magnet(s) and iron, and/or frictional surface elements located on corresponding structures of the cartridge 370 and/or receptacle 372.

In some embodiments, a reprogrammable RFID tag 394 may be positioned on the generator 320, fog cartridge 370, reservoir 374 and/or nebulizing module 386 for retaining and/or providing information. The information may include, but not limited to, any combination of the following: serial number, production date, expiration date, production plant, operation time, nebulizing module 386 cycles or runs, solution 10 identification (and/or constituents thereof), solution 10 concentration information, fluid levels, cartridge 370 design revision number and/or other information. The master controller 9, the dry fog control unit 360 or other control units described herein may read this information and determine whether the generator 320, fog cartridge 370, reservoir 374 and/or nebulizing module 386 should continue to be in operation, cleaned, repaired or replaced (e.g., expired fluids, incorrect fluids, fluid levels insufficient, etc.). Further the information may be used to control the operation of the system 1 and/or fog delivery system 300 generally by determining fog times, ratios of fluids, etc. The ability to read the information of the RFID tag 394 may be provided by a RFID reader 396 positioned on or near the fog receptacle 372 or hand-held device 397. The RFID reader 396 may detect the presence of a RFID tag 394, read the data stored on the RFID tag 394, and/or write over the data stored on the RFID tag 394. In combination with the master controller 9, the dry fog control unit 360 or other control units described herein, the RFID reader 396 may permit incrementing each nebulizing module 386 using sensory feedback loops.

In some embodiments, the dry fog generator(s) 320 may produce uniformly-sized droplets 302. In other embodiments, the dry fog generator(s) 320 include specialized spray nozzles that emit a spectrum of particle sizes within a droplet size range 304. The high surface tension of the droplets 302 having droplet size ranges 304 that have diameters less than 8 microns, IO microns or 20 microns, for example, may minimize the ability for water to condense on the surface of the droplets 302, thereby permitting water vapor to be more precisely controlled. Dry fog systems 300 and their resulting droplets 302 are designed to only agglomerate to airborne dust, not wet the surfaces 5 located in the environment 3 where the droplets 302 are being dispersed. For example, for a solution 10 being hypochlorous acid, the dry fog delivery system 300 may produce droplets 302 with a size range 304 under ten microns in diameter for minimizing water condensation on the droplets 302.

In the prior art, when solutions are nebulized, the droplets 302 generated tend to shrink in size as the percentage relative humidity in the environment 3 decreases (forming an inverted, negatively sloped curve when droplet size is on the y-axis and relative humidity is on the x-axis). The shrinkage of the droplet 302 when the relative humidity is low is due to evaporation of water in the droplet 302, the main constituent of many solutions 10. The decreasing size of the droplet 302 changes the chemistry within each droplet 302. For example, the concentration of other, non-water constituents increases as the droplet size decreases, possibly affecting the pH and reactivity within the droplet.

Figure 7:
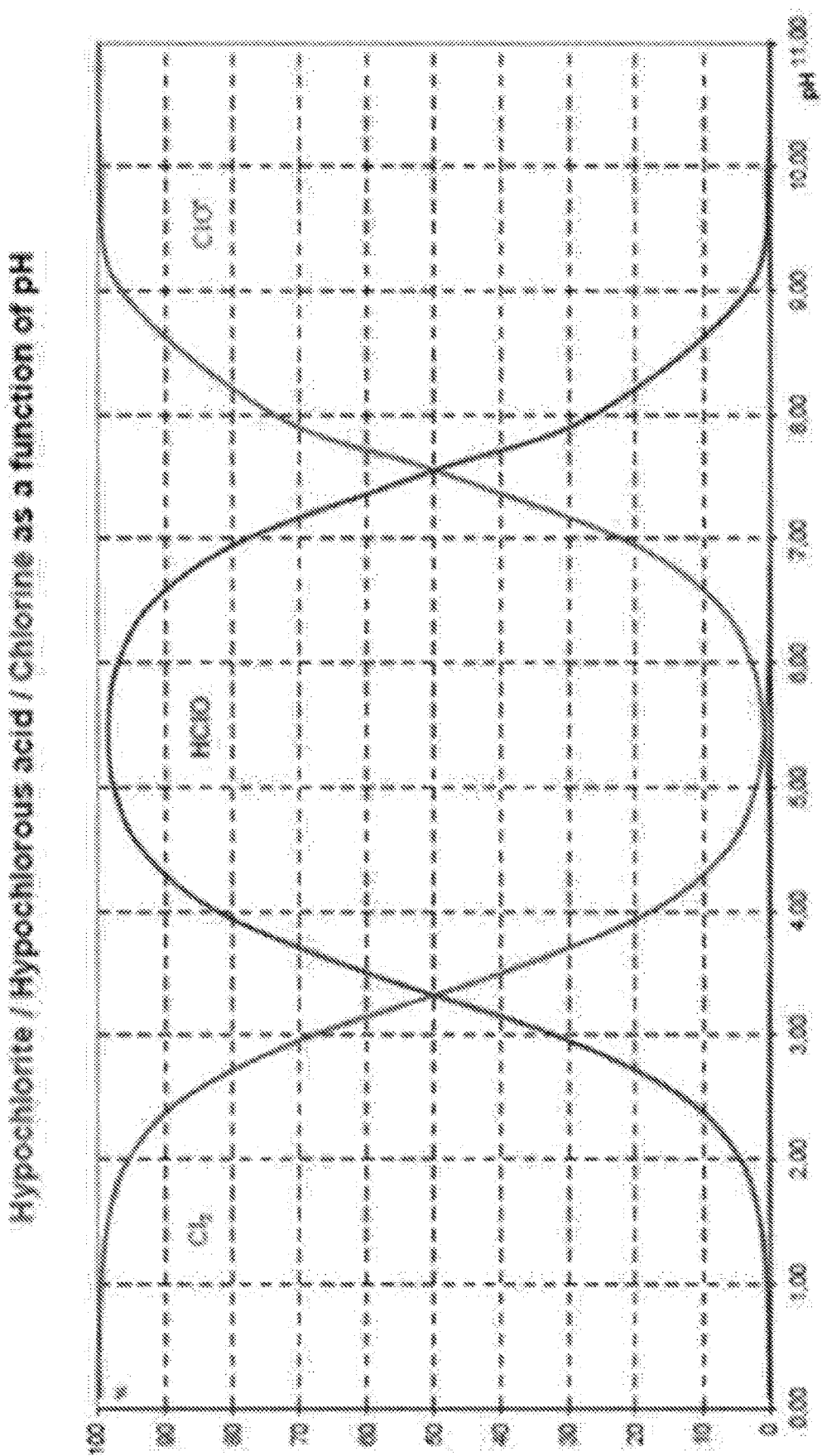
Figure 8:
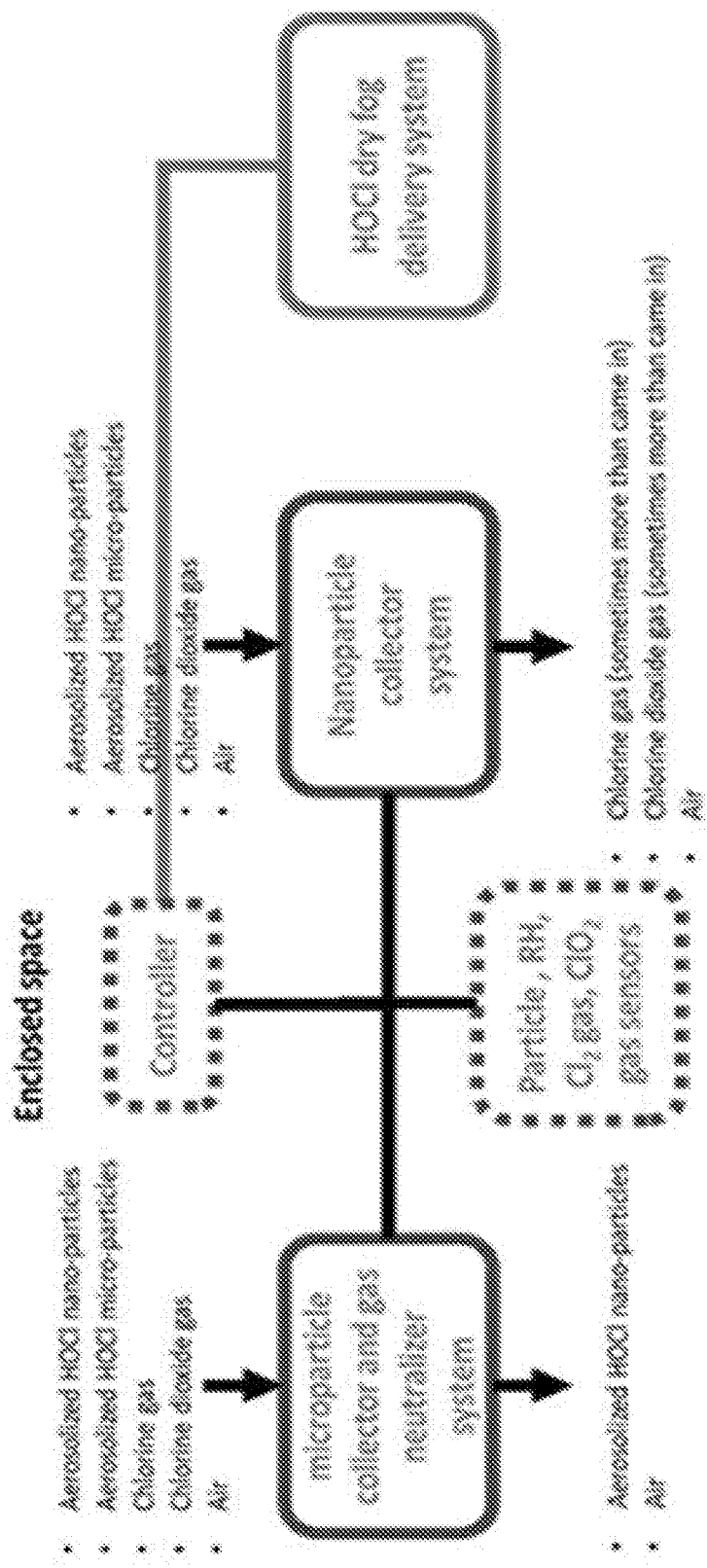
Figure 9:
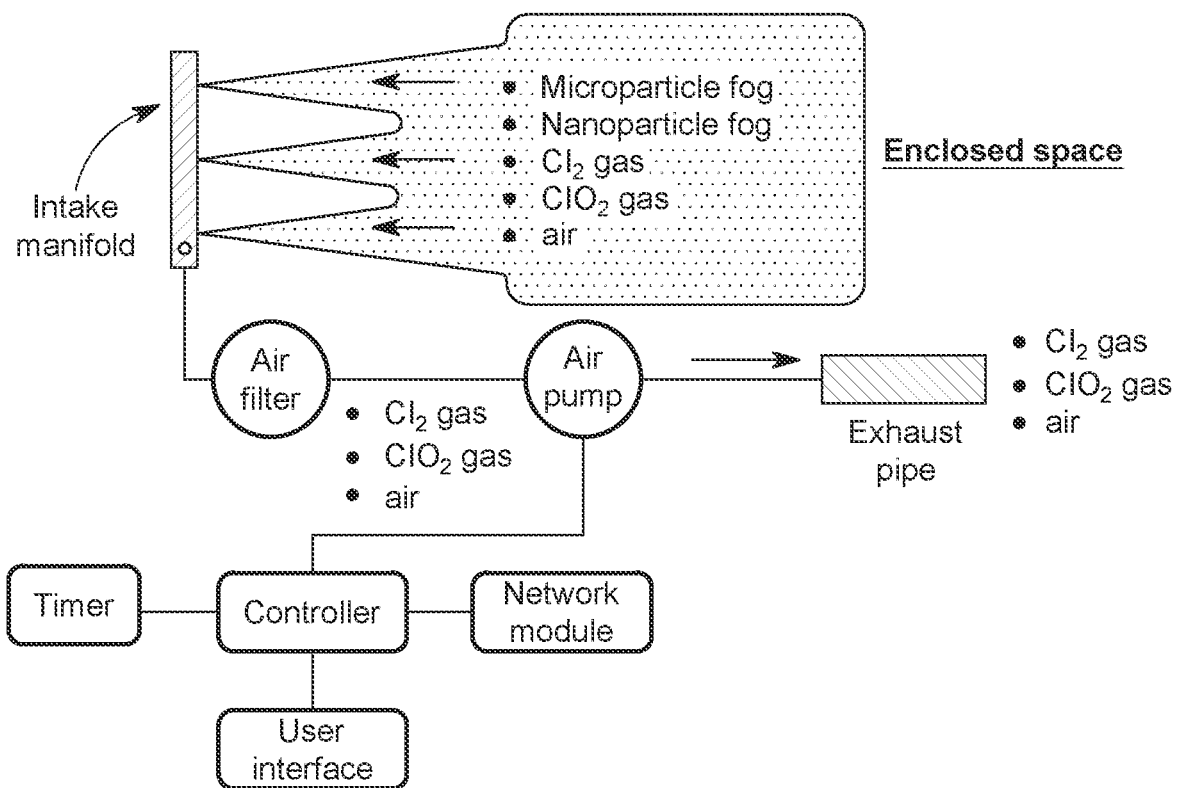
Figure 10:
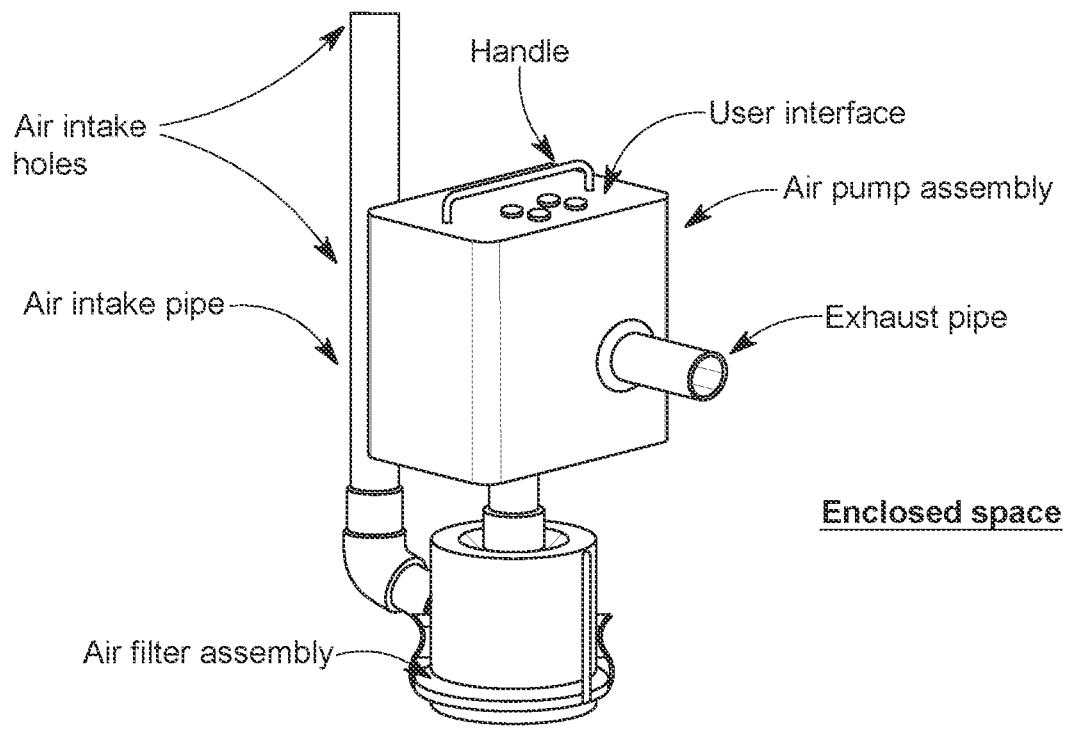
FIG. 10 is a perspective view of the particle collection system according to one or more embodiments of the present invention.
Figure 11:
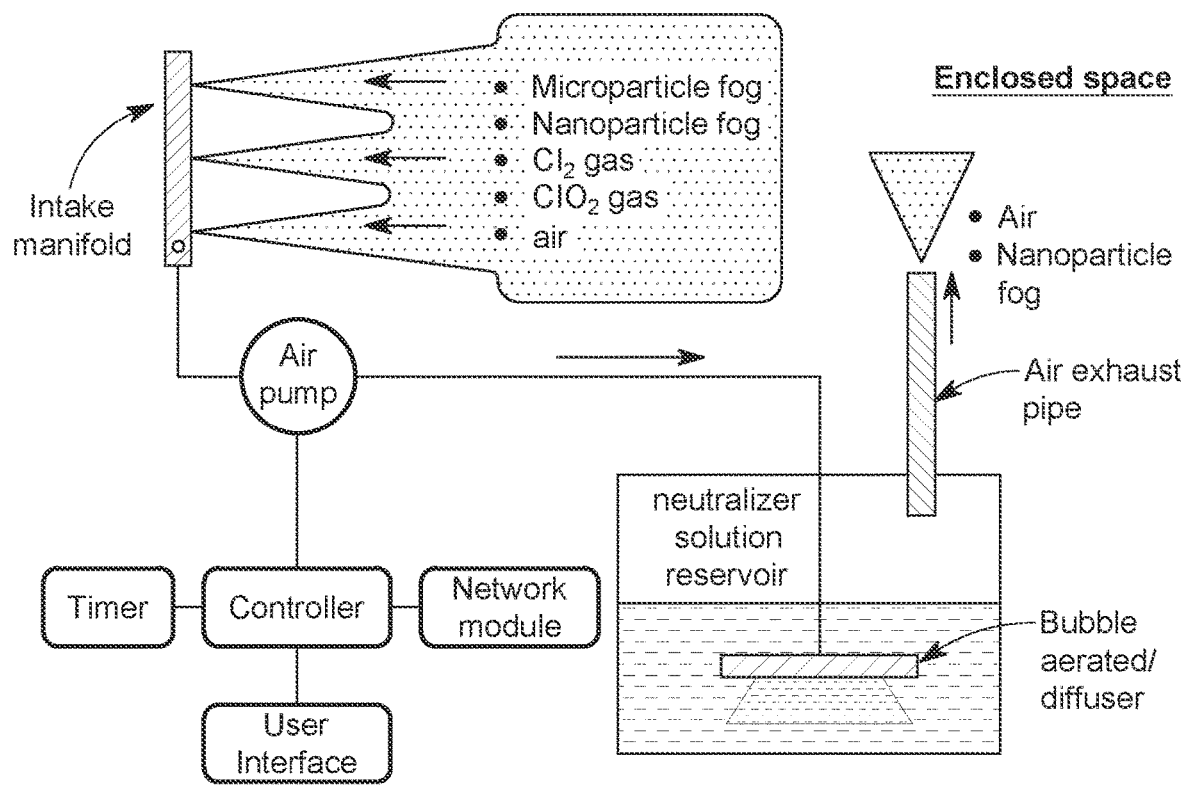
FIG. 11 is a schematic view of the gas collection system according to one or more embodiments of the present invention.
Figure 12:
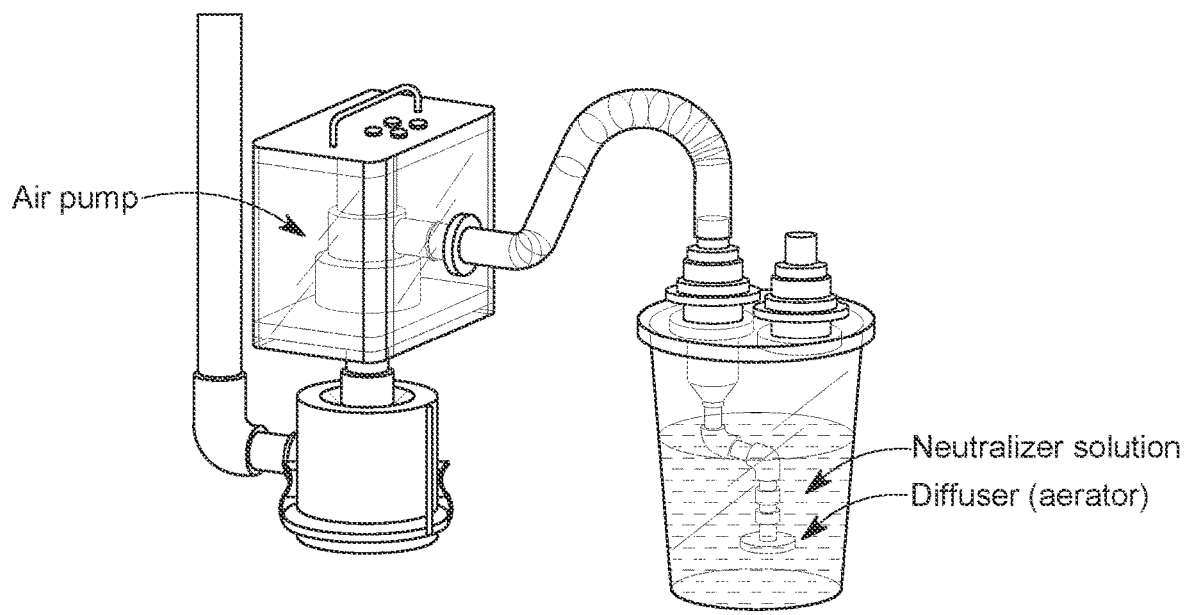
FIG. 12 is a perspective view of the gas collection system according to one or more embodiments of the present invention.
Figure 13:
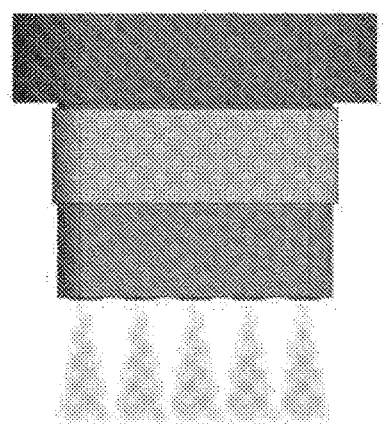
FIG. 13 is a front view of the fog cartridge dispersing fog according to one or more embodiments of the present invention.
Figure 14:
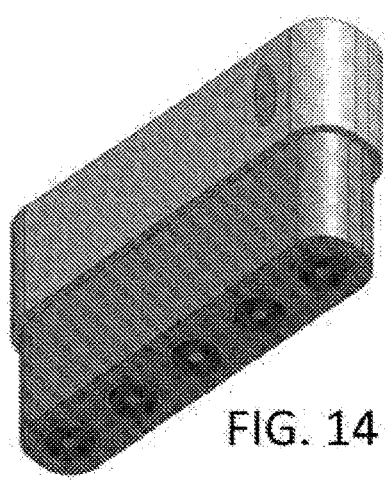
FIG. 14 is a perspective view of the nebulizing portion of the fog cartridge according to one or more embodiments of the present invention.
Figure 15:
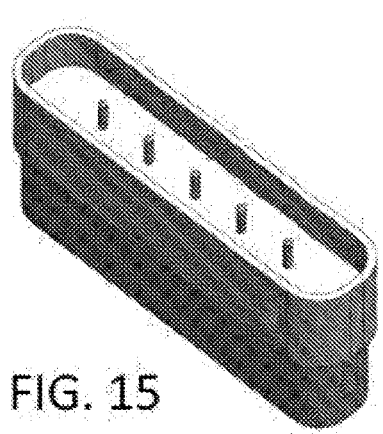
FIG. 15 is a perspective view of the nebulizing portion of the fog cartridge according to one or more embodiments of the present invention.
Figure 16:
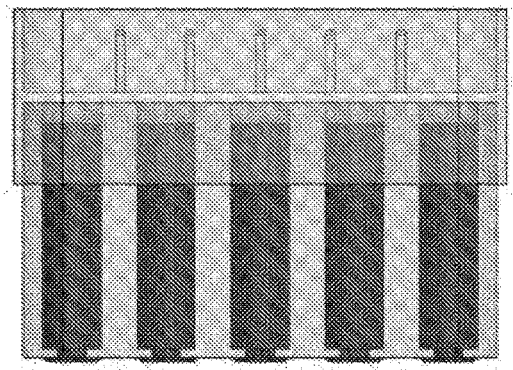
FIG. 16 is a front view of the nebulizing portion of the fog cartridge according to one or more embodiments of the present invention.
Figure 17:
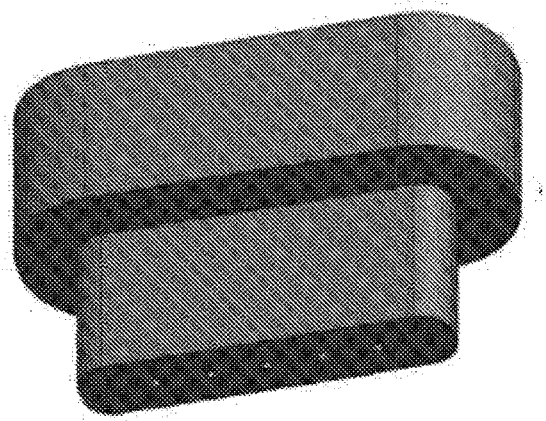
FIG. 17 is a perspective view of the engaging portion of the fog cartridge according to one or more embodiments of the present invention.
Figure 18:
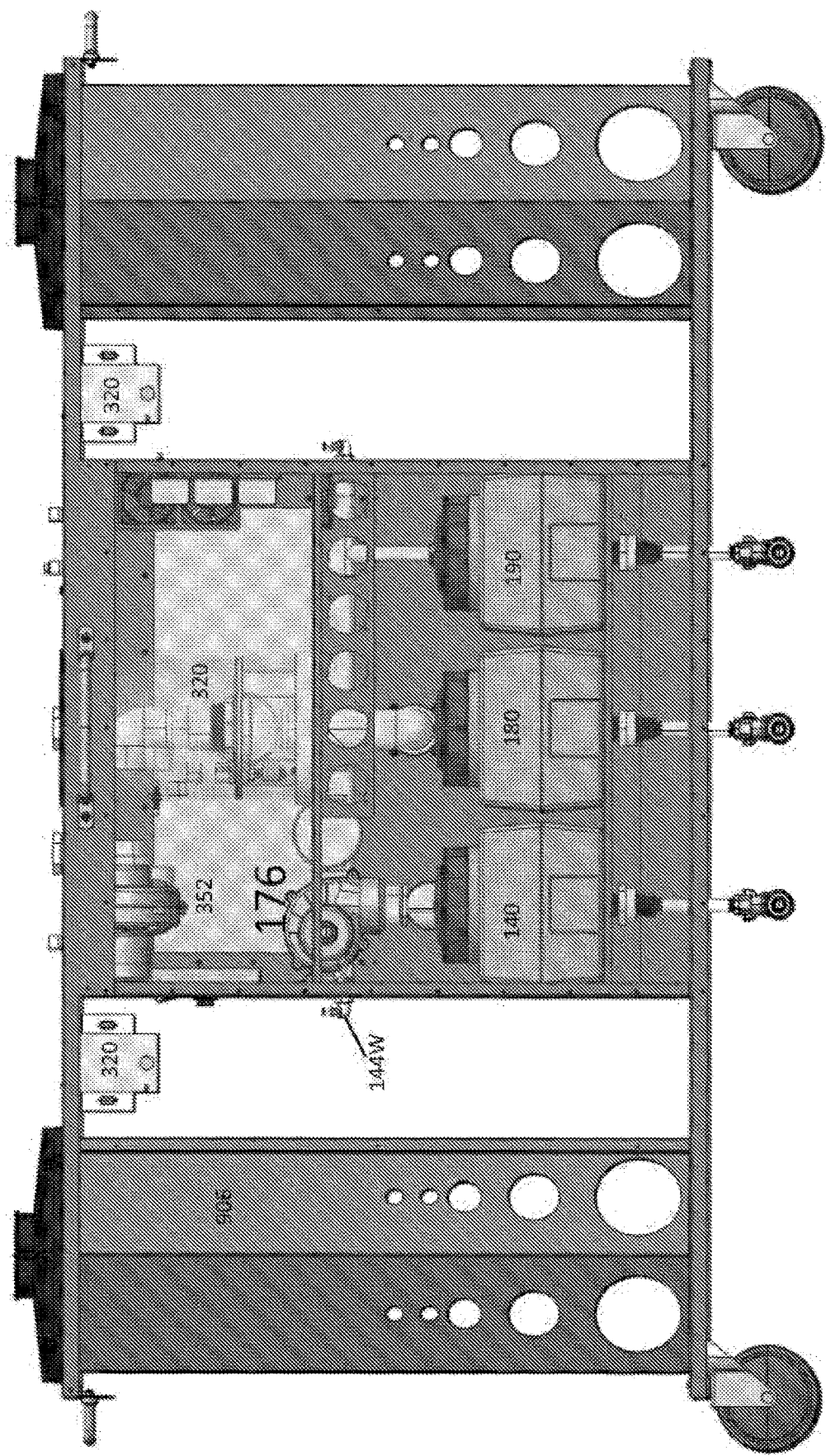
FIG. 18 is a back view of the mobile unit according to one or more embodiments of the present invention.
Figure 19:
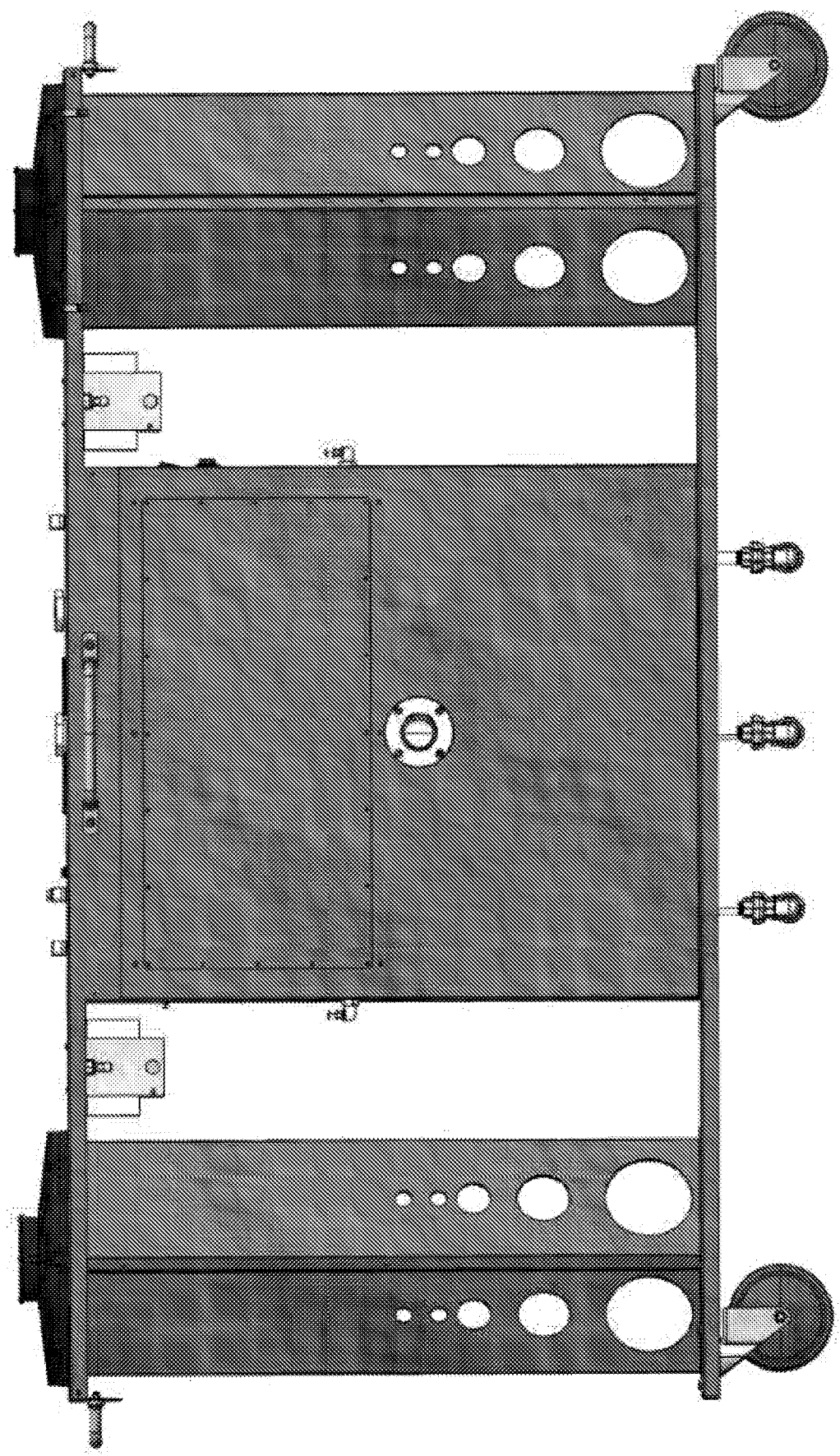
FIG. 19 is a front view of the mobile unit according to one or more embodiments of the present invention.
Figure 20:
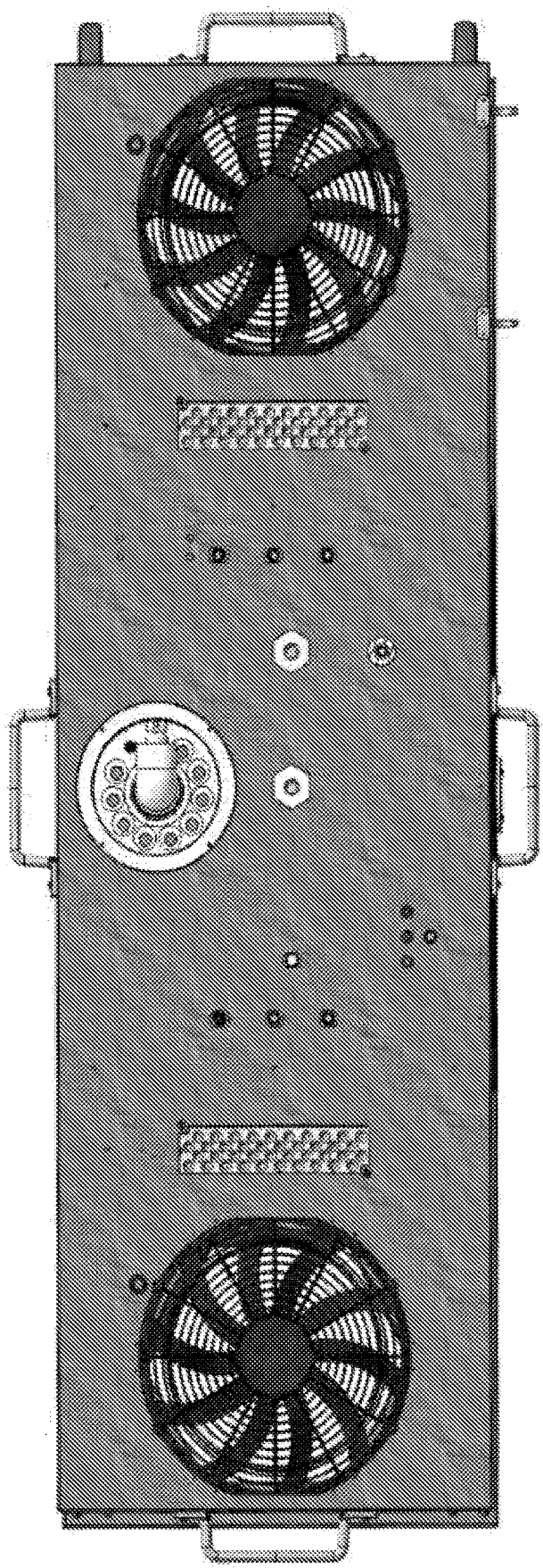
FIG. 20 is a top of the mobile unit according to one or more embodiments of the present invention.
Figure 21:
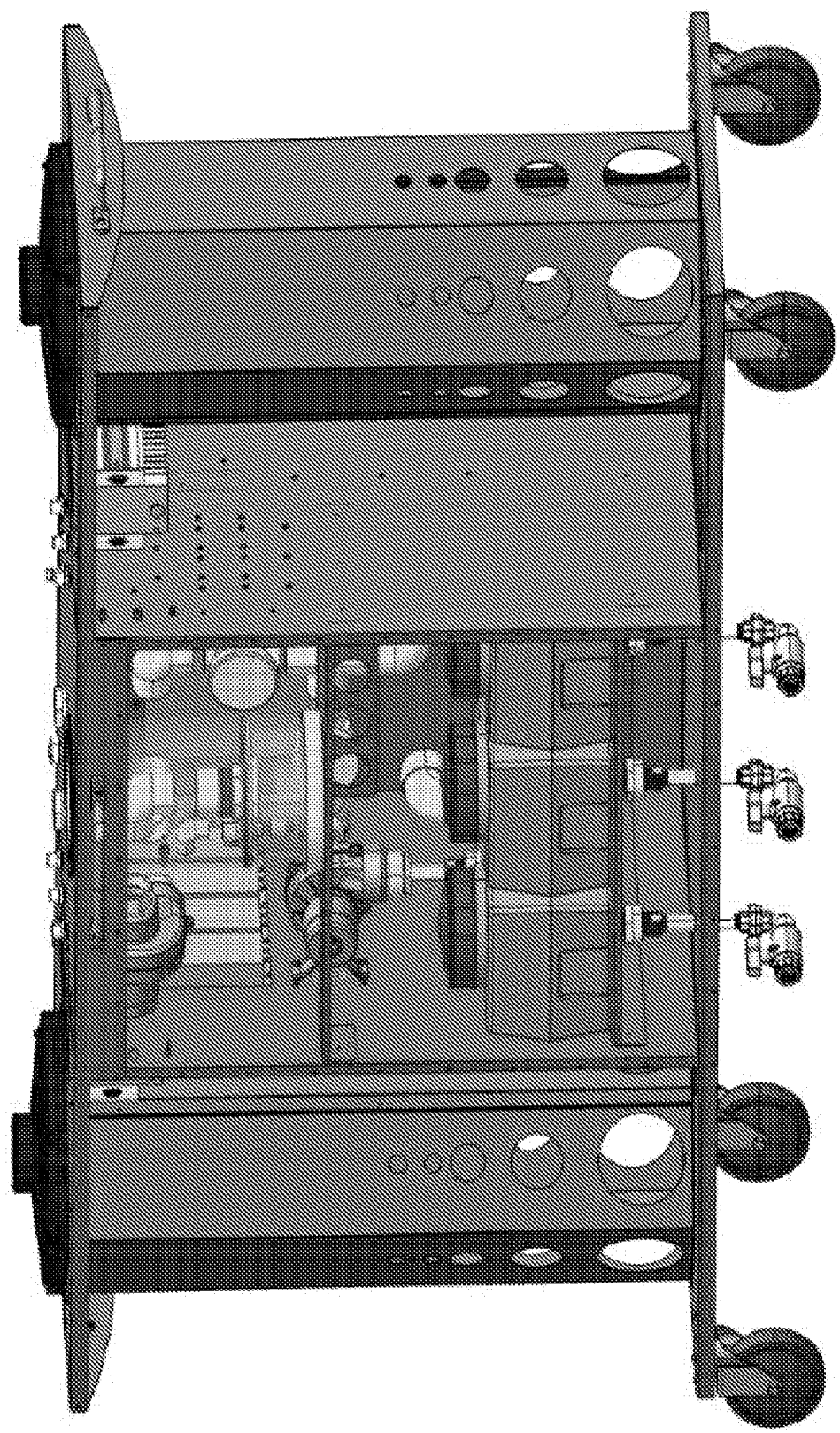
FIG. 21 is a perspective view of the mobile unit according to one or more embodiments of the present invention.
Figure 22:
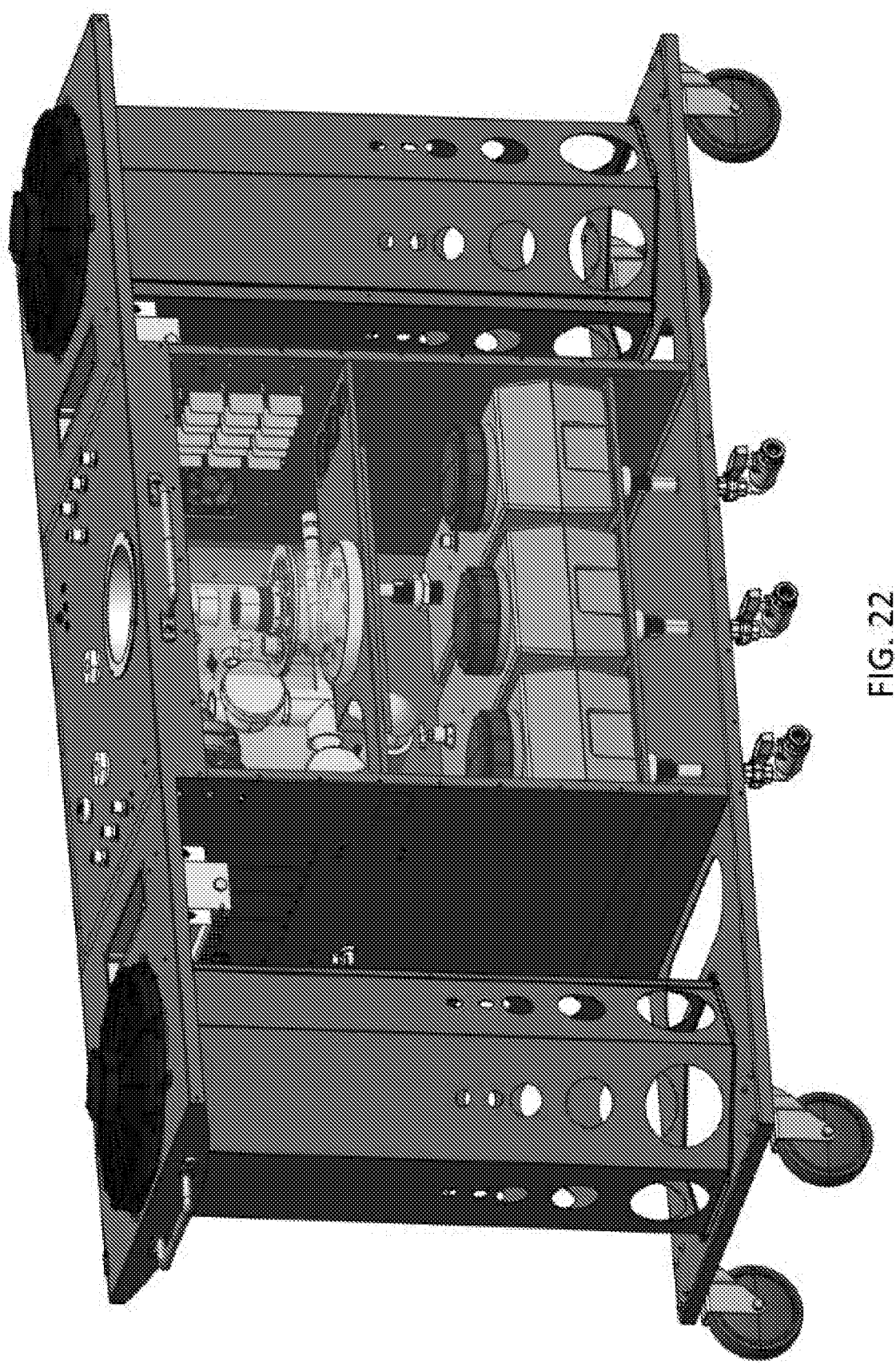
FIG. 22 is a perspective view of the mobile unit according to one or more embodiments of the present invention.
Figure 23:
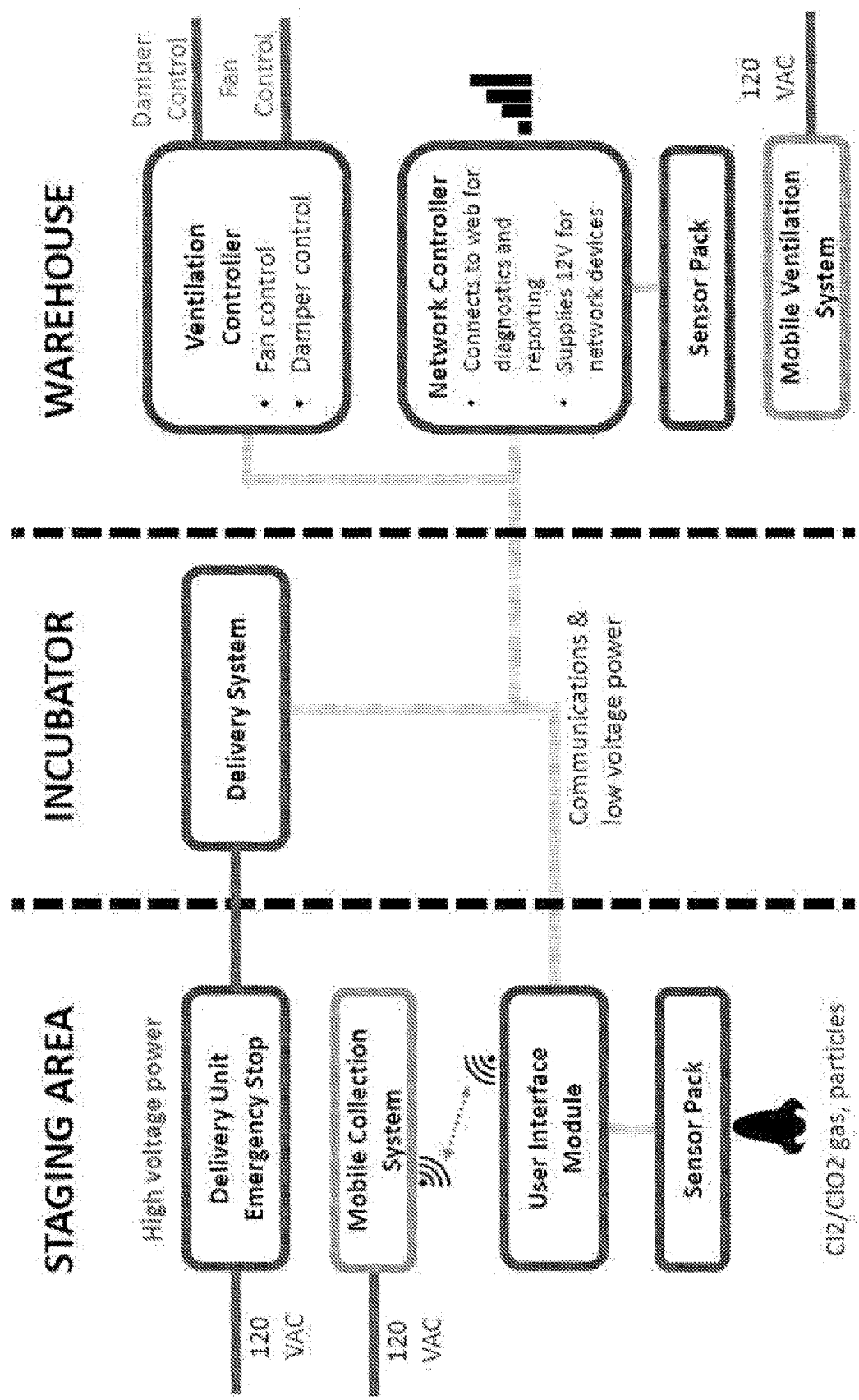
FIG. 23 is a schematic diagram of the communications of the system according to one or more embodiments of the present invention.

In the example of hypochlorous acid specifically, this increase in the concentration of the hypochlorous acid decreases the pH. Once the pH level of the hypochlorous acid droplet 302 crosses below the four pH threshold, for example, chlorine gas begins to form at a significant rate (as is evidenced by the free chlorine pH dissociation curve in FIG. 7) and is released from the droplet 302, creating a more hazardous environment 3. Further, these reactions result in the hypochlorous droplets 302 having less effectiveness, since the chlorine gas is heavier than air and tend to sink to the lowest point in a given environment 3, particularly when the environment is closed 3. As is depicted in the free chlorine pH dissociation curve, the optimal pH for a hypochlorous acid solution (from a fluid degradation and microbicidal perspective) is around 6 pH, with production of chlorine gas increasing as the pH drops and the concentration of hypochlorite (a less effective oxidant) increasing as the pH rises.

As disclosed throughout herein, various sensors 160 may be included throughout the system 1 and/or environment 3 for determining actual conditions 22. The sensed, actual conditions 22 may be wirelessly or electronically communicated or retrieved by the master controller 9 or any of the various control units of the system 1. Software may permit automated control of various components of the system 1. Further, indications may be made through various interfaces or display, light or sound indications for informing actual conditions 22 and recommended actions to a user for manual operation.

In some embodiments of the presently disclosed system 1, the dry fog delivery system 300 may incorporate various sensors 160. To measure when the solution 10 or environment 3 has a condition 2 and/or an actual condition 22, any component of the delivery system 300, fog tank 310, fog solution tank 350, water tank 336 may include one or more sensors 160. The one or more sensors 160 may be positioned within or on the delivery system 300 and/or delivery tank 310 or may insertable therewithin. One or more sensors 160 may be positioned with the environment 3. For example, two or more relative humidity sensors 160R may be included in various positions throughout a closed environment 3 for measuring the relative humidity within the environment 3. One or more of the sensors 160 may be housed together. Additional sensors 160 and their uses are described further herein and may be applied to the delivery system 300. In some embodiments, the delivery system 300 may include a pH sensor 160P, a temperature sensor 160T and/or a fluid level sensor 160F for sensing various conditions 2 (e.g., the fluid level, temperature and/or pH of the fog tank 310).

To measure when the environment 3, whether open or closed, meets a condition 2 being a relative humidity range (e.g., above 80%), the dry fog delivery system 300 may include one or more relative humidity sensors 160R for sensing the relative humidity of the environment 3.

Dry Fog Methods.

The presently disclosed dry fog delivery system 300 offers a solution to the issues of the prior art. Through the dry fog system 300, a solution 10 may be dispersed into the environment 3 in droplet 302 form. Droplets 302 of the solution 10 which accumulate on surfaces 5 of an environment 3, such as an eggshell, for example, may allow for the water of the droplet 302 to evaporate, thereby leaving a dry deposit on the surface 5. This deposit may serve to clean the surface 5 (when originating from a cleaning solution 10A, for example), protect the surface 5 (when originating from a cuticle solution 10B, for example) and/or enhancing the surface 5 (when originating from an enhancing solution 10C, for example). When the surface 5 is an eggshell, the leftover dry deposit of the solution 10 may permit the eggshell to continue to breathe through its pores. The dosage of the agents 14 and/or reagents 16 (and/or the constituents of the solution being mixed with water) may ensure that the density of constituents within the solution 5 permit breathing when the solution 10 dries on an eggshell surface 5. Similarly, the ratios of solutions 10 being dispersed in the same environment 3 may be controlled. Some of the leftover deposit constituents may be the same natural cuticle constituents found on eggshells when laid, or equivalents or derivatives with substantially similar qualities.

Experimentation has shown that the size shrinking rate of droplets 302 having solutions 10 constituting water is minimal when the relative humidity in an environment 3 crosses beyond the 80% threshold. Droplets 302 dispensed into the environment 3 when the relative humidity is at or above 80% remain roughly the same size. By increasing and maintaining the relative humidity in an environment 3 at or above 80%, dry fog dispersion of droplets 302 may be much more effective since the chemistry inside the droplet 302 remains stable.

Figure 6:
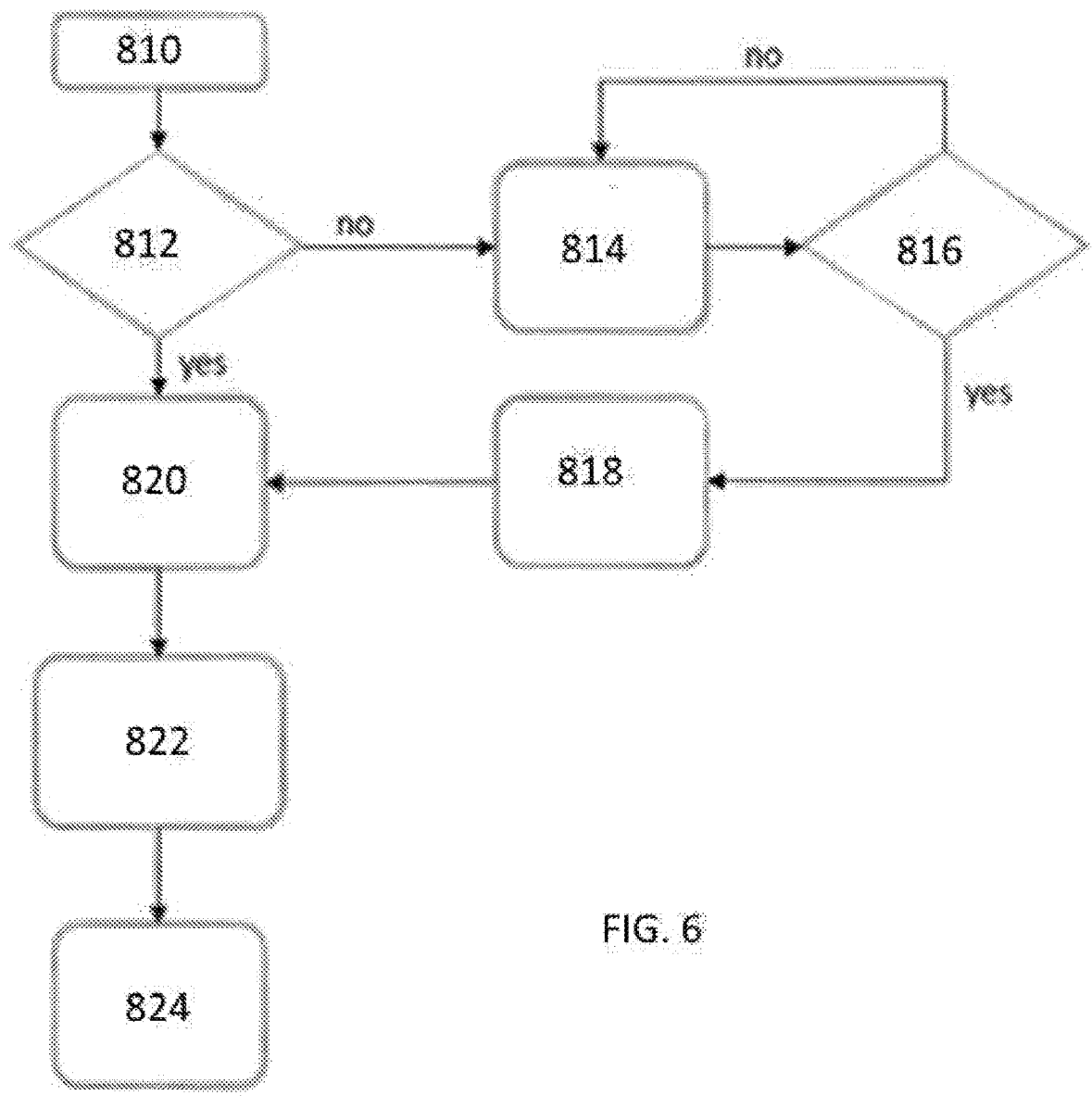

In FIG. 6, the system 1 may be initiated 810, then, through the use of one or more humidity sensors 160R positioned in the environment, determine if the actual condition 22 of the relative humidity of water falls within a condition 2 (e.g., greater than or equal to 80%) 812. If no, then the dry fog delivery system 300 may be engaged to deliver water droplets 302 into the environment 814. In some embodiments, after a period of time 822A, the delivery of water droplets may cease, then another determination of the actual condition 22 of the relative humidity may be made. A delay period of time 822B may pass before the determination is made following water droplet cessation. In other embodiments, the second determination may occur while the water droplets 302 are being delivered, and may again determine whether the relative humidity falls within a condition 2 816. If the relative humidity is determined to be within the condition 2, then the system may cease delivery of the water droplets 302 (in some embodiments) 818 and start the delivery of a solution 10 (e.g., HOCl solution) 820. After another period of time 822C, the delivery of the solution 10 dry fog may cease. Immediately, or after a final period of time 822D, the entire process of this paragraph may be repeated, and may be repeated any number of times.

According to some embodiments, the delivery system 300 further includes a humidifier 330 for dispersing water or a water-containing solution 332 into the environment 3 for increasing and maintaining a high relative humidity. The humidifier 330 may be sealingly engaged with a humidifier hose 334 for delivering the water solution 332 from the water solution tank 336. A humidifier pump and/or valve 338 may be positioned along the humidifier hose 334 or incorporated into the water tank 336 or humidifier 330 for effectuating the delivery of the water solution 332 through the humidifier hose 334. The humidifier 330 may be employed as a substitute for the dry fog generator 320 for creating water droplets 302.

In other embodiments, the fog tank 310 may be configured for dispersing both the solution 10 and the water solution 332. The fog tank 310 may further include a water reception aperture 312W for receiving the water solution 332 from a water tank hose 314W in sealed and fluidic engagement with a water tank 336. The water pump 338 may be positioned along the water tank hose 314W or incorporated into the water tank 336 or fog tank 310 for effectuating the delivery of the water solution 332 through the fog tank 310 to the generator 320.

In one embodiment of the dry fog system 300, a method of maintaining a condition 2 for the system 1, environment 3, solution 10, delivery system 300 and/or fog tank 310 is provided. The condition 2 may include a value or a specific range of values for one or more specific conditions (e.g., temperature, pH, humidity, time, concentration, fluid level, etc.). One or more of the sensors 160 may be employed to measure various conditions 2. An actual condition 22 may be directly measured or maybe calculated or determined by the dry fog control unit 360 (or any other control unit or the master control unit 9) using one or more of the other conditions 2. If the actual condition 2 matches, or falls within, the condition 2, the delivery system 300 may remain unchanged for a waiting period 822P. If the actual condition 22 does not match, or falls without, the condition 2, one or more components of the delivery system 300 may be changed through an action 4.

According to some embodiments, the dry fog delivery system 300 includes a dry fog control unit 360. The dry fog control unit 360 may be in wireless and/or electrical communication with various sensors 160, the fog delivery generator 320, the humidifier 330, the water pump 338, the fog solution pump 338, and/or other components of the fog system 300 or system 1. In a dry fog system 300 including a humidifier 330 or dry fog generator 320 in fluidic engagement with a water tank 336 for dispersing the water solution 332 into an environment 3, the dry fog control unit 360 may be in wireless and/or electrical communication with a relative humidity sensor 160R and the humidifier 330 and/or dry fog generator 320.

According to at least one method embodiment, the dry fog control unit 360 determines, via one or more relative humidity sensors 160R, whether the actual condition 22 being relative humidity of the environment 3 falls within a condition 2 (e.g., greater than 80% relative humidity). If the actual condition 22 falls within the condition 2 then a waiting period 822P may pass before another determination. If the actual condition falls without the condition 2, then the dry fog control unit 360 may activate the humidifier 330 or dry fog generator 320 (and/or water pump 338) for dispersing the water solution 332 into the environment 3 for a specified period of time, thereby attempting to increase the relative humidity of the environment 3 to within the condition 2. These methods steps may be repeated.

According to at least another method, the dry fog control unit 360 first determines, via one or more relative humidity sensors 160R, whether the actual condition 22 being relative humidity ofthe environment 3 falls within a condition 2 (e.g., greater than 80% relative humidity). If the actual condition 22 falls within the condition 2 then the control unit 360 activates the dry fog generator 320 (and/or fog solution pump 352) for dispersing the solution 10 into the environment 3 for a specified period of time. Once the dispersal of the solution 10 is ceased, another actual condition 22 determination is made by the dry fog control unit 360. If, again, the actual condition 22 falls within the condition 2 then the control unit 360, again, activates the dry fog generator 320 for a specified period of time. If, however, the actual condition 22 falls without the condition 2, then the dry fog control unit 360 may activate the humidifier 330 or dry fog generator 320 for dispersing the water solution 332 into the environment 3 for a specified period of time, thereby attempting to increase the relative humidity of the environment 3 to within the condition 2. Once the water solution 332 dispersal ceases, another actual condition 22 is made. If, again, the actual condition 22 falls without the condition 2, the water solution 332 dispersal repeats. If, however, the actual condition 22 falls within the condition 2, the solution 10 dispersal is effectuated by the dry fog control unit 360.

The methods described in the preceding paragraph ensure that the dispersal of the water solution 332 may not run simultaneously with the solution 10 dispersal, thereby minimizing the undesired reaction of water with the solution droplets 302 (e.g., creating chlorine gas when the solution 10 is hypochlorous acid).

In some embodiments of the present invention, a number of solutions 10 may be dispersed as droplets 302 via the dry fog system 300 simultaneously, sequentially, in alternating rotations or some combination thereof, through a plurality of generators 320 and/or nebulizing modules 386. Such methods of the dry fog system 300 may be combined with methods incorporating the humidifier 330 or other systems 100, 200, 400 for effectively applying a cleaning solution 10A, cuticle solution 10B and/or enhancing solution 10C to a surface 5.

Byproduct Collection and Neutralization.

According to further embodiments of the disclosed system 1, once a solution 10 is dispersed via droplets 302 by the dry fog delivery system 300 within an environment 3, the solution 10 may interact with the environment 3 and/or decompose over time to create fog byproducts 602 (e.g., chlorine gas or chlorine dioxide gas). The system 1 may further include a collection system 400 for collecting and/or neutralizing the solution 10, byproducts 602 and/or air 6 of the environment 3. The environment 3 may be closed or sealed. Fog byproducts 602 may include, for example, nanoparticles, micro particles, gases and/or air.

Some regulatory agencies, such as the U.S. Environmental Protection Agency, require the registration of a some solutions 10 if it is to be produced and distributed from a central location. The tests required for the registration of a biocide for fogging applications, for example, are more elaborate and pricier than for surface cleaning applications. Therefore, it may be advantageous to contend that aerosols, harmful or otherwise, remain in the sanitized or disinfected space after the application of fog and the fog's removal, as is disclosed by the systems and methods described herein.

According to one embodiment, as is depicted in FIGS. 8-12, the collection system 400 may include a gas collection system 402 for collecting and neutralizing gas and/or microparticles. The collection system 400 may include a particle collection system 404 for collecting and neutralizing nanoparticles and microparticles. A collection control unit 440 may be utilized by the collection system 400 for controlling the particle and gas collection systems 404, 402, accepting sensed information from the sensors 160, and/or making determinations based on the sensed information.

The particle collection system 404 may include an particle intake manifold 410 containing any number of intake apertures 412 for collecting air 6 from the environment 3. The air 6 may include droplets 302, solution 10, fog byproducts 602 and/or other constituents of the environment 3. The intake manifold 410 may be in fluidic communication with an air filter assembly 414 including one or more air filters 416 or may contain one or more air filters 416 therein. The intake manifold 410 and/or air filter assembly 414 may be in fluidic communication with an air pump assembly 420 including an air pump 422 or may contain an air pump 422 therein. In some embodiments, the air filter assembly 414 may also include an air pump 422. In such embodiments, the particle collection system 404 may collect microparticles, nanoparticles and gases and exhaust the gas, through an exhaust pipe 424 engaged with the intake manifold 410 or air pump assembly 420 or air filter assembly 414.

The gas collection system 402 may include an gas intake manifold 430 containing any number of intake apertures 432 for collecting air 6 from the environment 3. The air 6 may include dry fog droplets 302, solution 10, fog byproducts 602 and/or other constituents of the environment 3. The intake manifold 430 may be in fluidic communication with an gas air pump assembly 440 including an air pump 442 or the manifold 430 may contain an gas air pump 442 therein. The gas collection system 402 may also include a neutralization tank 450, housing a gas neutralizing reagents 458, and in fluidic communication with the manifold 430 and/or the air pump assembly 440 via a gas collection hose 452 extending through a gas collection aperture 454 of the neutralization tank 450. The gas collection hose 452 may include a gas collection diffuser 454 thereon for aerating the collected air 6 and neutralizing certain gases therein, such as chlorine gas or chlorine dioxide. The neutralization tank 450 may include an exhaust pipe or aperture 456 for exhausting the remaining air 6 therefrom, including any nanoparticles contained therein that may not have dissolved in the gas neutralizing reagents 458. In such embodiments, the particle collection system 404 may collect microparticle fog, nanoparticle fog and gases and exhaust gas, through an exhaust pipe 424 engaged with the intake manifold 410 or air pump assembly 420 or air filter assembly 414.

In alternative embodiments, the gas intake manifold 430 may be in fluidic communication with an air filter assembly 434 including one or more air filters 436 or may contain one or more air filters 436 therein so that the gas collection system 402 may also collect and neutralize nanoparticles. In such an embodiment, the air filter assembly 434 may be in fluidic communication with an air pump assembly 440.

The air filters 416, 436 may by a HEPA filter.

The operation of the collection system 400 may be concurrent or sequential, and/or may be in coordination with control units for matching conditions 2. In some embodiments, the operation ofthe gas collection system 402 and/or particle collection system 404 may be solely based on time, with each or both operating for certain lengths of time and resting for other lengths of time.

In some embodiments the dry fog system 300 may be run in coordination with the collection system 400. For example, the dry fog system 300 may be initiated and ran for a set time period, after which the collection system(s) 400 may be initiated and ran for another set time period. Once the first cycle of fogging, neutralizing and collecting is completed, the environment 3 may be disinfected or sanitized for further removing concentrations of nanoparticles, microparticles, chlorine gas and chlorine dioxide gas, so that these concentrations do not exceed unsafe levels. In some embodiments, the collector systems 400 may not run in unison but may have staggered and/or alternating time periods, with concurrent and/or sequential runs.

Feedback-based operations rely on feedback algorithms for running the dry fog system 300 and/or the collection system(s) 400. For example, the dry fog system 300 may run for a period regulated by a feedback algorithm tuned to achieve a specified level of disinfection or sanitation. The algorithm may consider the type of microbes being targeted, the specified microbial load reduction to be achieved, the concentration of droplets 302 in the environment 3 and dwell period, the relative humidity over the disinfection or sanitation period, and other information. The dry fog system 300 and/or collection system(s) 400 may run concurrently to reduce chlorine gas and chlorine dioxide gas levels in the environment 3 during the dry fogging. In this mode, the operator may be notified that the disinfection or sanitation cycle is complete via a wireless user interface, alarm system or through a visual indicator.

The collection system(s) 400 may be capable of removing microparticle fog, neutralizing chlorine gas, and/or neutralizing chlorine dioxide gas. In some embodiments, nanoparticles may be encapsulated inside small, aerated bubbles, instead of being dissolved into the neutralization reagents 458. In such cases, these nanoparticles may escape back into the atmosphere. An inline filter may be provided for capturing these nanoparticles and removing them. In other embodiments, the filter assembly may remain empty. The nanoparticle fog may be generated as a result of the evaporation that occurs when of microparticle fog that is generated in low RH conditions(<80% RH).

An additional tank 470 maybe daisy-chained to the first neutralization tank 450 to prevent the splashing and exit of neutralization reagents 458 into the environment 3 during operation.

To prevent the release of too much of too much gas into the environment 3, a control unit may activate the pump 422, 442 intermittently.

In some embodiments, the collection system(s) 400 may be provided for removing micron and submicron sized aerosolized particles from the environment 3, which may be hazardous if inhaled. The fog collection systems 400 may utilize a HEPA or other type of air filter 404 and an inline air pump 406. When the fog collection system 400 is in operation, it may pull air from a closed environment 3 into the air filter 404 and returns clean air. The air pump 406 may run for a time period 822 determined according to the particle count sensed inside the environment 3 for preventing hazardous conditions. Control units and/or sensors 160 may monitor the use of the fog collection system 400, which may include sensing the cycle count, particle accumulation and/or collection, determining the need for air filter 404 replacement, or locking the system 400 down when hazardous conditions are present.

EXAMPLE 5. The neutralizer solution (sodium thiosulfate, sodium hydroxide and water), when combined with HOCl may undergo multiple reactions with free and combined chlorine, depending on the solution pH. The amount of sodium thiosulfate required for neutralization may vary with solution pH. Any hydrochloric acid produced may be salted out by the sodium hydroxide ($HCl+NaOH \rightarrow NaCl+H2O$).

$$Na2S2O3+4HOCl+H2O \rightarrow 2Na2SO4+4HCl$$

$$Na2S2O3+HOCl \rightarrow Na2SO4+S+HCl$$

$$2Na2S2O3+HOCl \rightarrow Na2S4O6+NaCl+NaOH$$

Chlorine gas in the neutralizer solution produces hydrochloric acid (HOCl). HOCl may be neutralized, as shown above. As stated, any hydrochloric acid produced may be salted out by the sodium hydroxide.

$$Cl2+H2O \rightarrow HCl+HOCl$$

Chlorine dioxide gas in the neutralizer solution produces sodium bisulfate and hydrochloric acid. As stated above, any hydrochloric acid produced will be salted out by the sodium hydroxide.

$$Na2S2O3+ClO2 \rightarrow Na\ HSO4+2HCl$$

Methods of Using the System.

Numerous methods of using the system 1 have been disclosed herein. The various subsystems 100, 200, 300, 400 of the system 1 may be used together—concurrently, sequentially, in rotation or cycles, or a mixture of these. The various sensors 160 and control units 9, 220, 360 or other control units of the system 1 may coordinate and communicate to automate methods or indicate manual instructions for methods. Timing schedules may be determined and/or used to control operation. Using sensed actual conditions 22, information and determined data, the operation may be controlled.

One embodiment of a method of the system 1 disclosed above was the coordination ofthe dry fog system 300 and the collection system 400. In some embodiments, the dispersal and collection of several solutions 10 may be enabled by the system 1. For example, a cleaning solution 10A, such as hypochlorous acid, may be dispersed by the dry fog system 300. During such dispersal (or immediately following or following after a period of time 822), the collection system 400 may be utilized for collecting particles and/or neutralizing gases. Sensors 160 of the system 1 may detect the actual conditions 22 of the environment (e.g., humidity, particle counts, and/or gas concentrations) to determine a starting time for the dry fog system 300 to disperse a second solution 10B for applying an artificial cuticle. The production system 100 and/or preservation systems 200 may be similarly controlled in coordination with this dispersal. Similar to the collection and neutralization of solution 10A, the system 1 may sense and control collection and neutralization of solution 10B. These processes may be repeated for an enhancing solution 10C, for multiple applications of the solutions 10A and/or 10B, or for cycling through repeated sequential processes.

In some embodiments, differing dosages of distinct solutions 10 may be dispersed. One advantage of including separate reservoirs 374, tanks or compartments for housing differing solutions 10 is for permitting various dosages of each solution 10 to be controlled individually, so that ratios of the solutions 10 to each other may be altered accordingly. Fluid level and fluid flow sensors 160 and controllers may be engaged for managing this process. For example, two different solutions 10 may be dispensed at a 3:2 or 4:1 ratio, three different solutions 10 may be dispensed at 2:2:1 ratio, or four different solutions 10 may be dispensed at a 2:1:1:1 ratio.

Generators 320 and/or nebulizing modules 386 may be wired in parallel if driven by the same driver circuit. The piezo driver may have a current sense signal capable of being converted to a digital value via an analog to digital converter circuit. The master controller 9, a dry fog control unit 360 or other control units described herein may control the operation the generators 320 and/or nebulizing modules 386 to ensure certain ratios are maintained.

According to some embodiments, the control units of the system 1 may track, through sensors 160 for example, the cycle count of the generators 320 and/or nebulizer modules 386 and the age of the solution 10 to determine the length and initiation of a dry fog dispersal. Over time the generators 320 and/or nebulizing modules 386 may generate fewer dry fog droplets 302. Similarly, some protein and or enzyme solutions lose their antimicrobial properties as a function of age. The system 1 may be controlled to disperse solutions 10 for achieving specific levels of microbial load reduction. Such control may be effectuated by modifying the length of time of dry fog dispersal of one or more solutions 10, which may take into account a number of sensed actual conditions 22 or determinations (e.g., cycle count of modules 386 and age of the fluid). The age of the fluid may be determined by reading the product date and time on the RFID tag 394 and comparing it to the actual time based on the time and date data provided by a real time clock module. The system 1 may also receive date and time data from the network communication module.

Mobile and Retrofit Systems.

Poultry breeder farms of the prior art may have numerous configurations. Breeder farms may collect broiler and parent stock eggs off a conveyor system that moves eggs from the farm to a control room. This process may also be done manually. Farm personnel may remove debris from the eggs using various methods and place the eggs in a flat. A number of the flats may be placed on a buggy and/or pallet 30. The buggies and/or pallets 30 may be placed in one or more temperature-controlled egg storage rooms (i.e., a sealable environment 3) until the buggies and/or pallets 30 may be taken to the hatchery or a centralized egg distribution center (also referred to as an egg depot).

Commercial egg incubators, for example, are typically sealable enclosures 3, 700 capable of housing the system 1 for applying aerosol solutions 10 to pallets 30 of eggshells 5 for cleaning, protecting and enhancing the egg during the incubation period through hatch. The system 1may be housed with the sealed enclosure 3, 700 or a pre-existing sealable environment 3 may be retrofitted to enable the system's functionality. Most commercial incubators contain a mobile environmental control unit that may be replaced with a modular version of the system 1.

The system 1 may include a sealable chamber 700 or may be positioned within and about a pre-existing sealable environment 3. A sealable chamber 700 and sealable environment 3 ensures that gas exchange there without is controlled. The sealable chamber 700 or sealable environment 3 may be configured to accept individual egg flats, buggy and/or pallets 30 of the poultry industry. The chamber 700 may include a chamber door 702 for selectively sealing and unsealing the chamber 700. The chamber 700 may be fixed or mobile. The doors 702, when closed, may include gasket (s) for sealing the door perimeters. In some embodiments, door sensors and actuated locks 705 may be employed to ensure the sealed chamber is sealed during operation, whether operated manually or automatically through a controller and/or interface. Solenoid door locks 705 may be provided and may be controllable via one of the controllers for sealing the chamber 700 during operation.

The system I or a pre-existing environment 3 (e.g., a commercial incubator) may include an exhaust or ventilation system 704 in sealed and fluidic communication with the chamber 700 or sealed environment 3. The exhaust system 704 may include an exhaust fan 706 for creating air flow and a exhaust damper 708 actuatable between an open and closed state for permitting fluid flow between the exhaust system 704 and the chamber 700 or sealed environment. The chamber 700 and/or sealed environment 3 may include one or more user interfaces 710.

The system 1 may include any combination of subsystems 100, 200, 300, 400, and may further include various sensors 160 and/or control units. The system 1 may be a modular unit, capable of being transported in and out of chambers 700 or sealed environments 3. In other embodiments, components of the system 1 may be modular (e.g., production system 100, preservation system 200, fog system 300), while other components may be affixed within, to or about the chamber 700 or sealable environment 3 (e.g., sensors 160, control units, user interface 710, collection system 400). In some embodiments, the environmental control unit of the prior art commercial operations may be retrofitted with certain components of the system 1.

In some other embodiments, various subsystems 100, 200, 300, 400 may be positioned and installed within, to or about the chamber 700 or sealable environment 3. For example, the fog delivery generator(s) 320, nebulizing modules 386, and/or humidifier 220 may be positioned within the environment 3 or chamber 700 on or near a ceiling or top surface and/or proximal the door(s) 702 for delivering dry fog within the environment 3 or sealed chamber 700.

Once a buggy and/or pallet 30 is loaded with eggs, and the environment 3 or chamber 700 is sealed, the system 1 may automatically initiate methods to treat the eggs with dry fog applications.

According to at least one embodiment of the present invention, the collection system 400 may include an intake manifold 410, 430 within the chamber 700 or sealed enclosure 3 for collecting the air, gas and/or particles within the chamber 700 or sealed enclosure 3. The intake manifold 410, 430, or the hose extending therefrom, may pass through a wall of the chamber 700 or sealed enclosure 3 for fluid communication with other components of the collection system 400 located outside the chamber 700 or sealed enclosure 3. Further, the system 400 may include an exhaust pipe 456 for permitting discharge of the remaining air, gas and/or particles remaining after collection and/or neutralization back into the chamber 700 or sealed enclosure 3. The exhaust pipe 456 may pass through a wall of the chamber 700 or sealed enclosure 3 for fluid communication with other components of the collection system 400 located outside the chamber 700 or sealed enclosure 3.

In yet another embodiment, the intake manifold 410, 430, or the hose extending therefrom, may pass through a wall of the chamber 700 or sealed enclosure 3 for fluid communication with a mobile version of the remaining components of the collection system 400.

In alternative embodiments, the entire collection system 400 may be housed within the chamber 700 or sealed enclosure 3. Once the sensors 160 detect, or control units determine, that certain conditions 2 are met, the exhaust system 704 may be controlled to exhaust any remaining air, gas and/or particles within the sealed chamber 700 or environment 3. In some embodiments, there is no collection system 400, only an exhaust system 704. In other embodiments, the collection system 400 is in fluid communication with the exhaust system 704 opposite the damper 708 for collecting and/or neutralizing the air, gas and/or particles after being exhausted from the chamber 700 or environment 3.

One embodiment of the present disclosure include components of the system I configured and positioned on a mobile unit 900. As is depicted in FIGS. 18-22, the mobile unit 900 may have wheels 901 for easing transport. The mobile unit 900 may include a base 902, a top 904 and one or more intake stacks 906 extending between the base 902 and top 904. An intake stack 906 may include one or more perforations 910 along the surface(s) 912 extending between the base 902 and top 904. An intake stack 906 may further include a fan 914 positioned proximal the top 904 and parallel, or substantially parallel, thereto. The fan 914, when in motion, may draw air through the perforations 910, upwards through the intake stack 906, through the fan 914 and towards a top area of the chamber 700 or environment 3. Micro aerosol particles between two and ten micrometers will tend to fall to a bottom of an enclosure, particularly when dry, which increases the probability of particle merge which may create a wet fog. The perforated intake stack 906 and its fan 914 move air, gas and/or particles at the bottom of the chamber 700 or environment 3 to the top 904. The speed of the fan 914 may be controlled to create homogeneous particle concentration throughout the chamber 700 or environment 3. Large fan blades and low fan speeds will help to minimize the risk of denaturing high molecular weight compounds through the transfer of high kinetic energy from the blade to the molecule. The perforations 910 proximal the base 902 may be larger than perforations 910 more distal the base 902 for encouraging the cycling of larger particles located falling to the bottom or floor of the chamber 700 or environment 3. In some embodiments, the perforations 910 are smaller the further they are from the bottom or floor.

The mobile unit 900 may include any components or subsystems 100, 200, 300, 400 of the system 1. In one embodiment, the collection system 400 is housed between the base 902 and top 904 of the unit 900. The intake manifold 410, 430 of the collection system 400 may extend from the unit 900. The manifold 410, 430 may include a section 920 extending from an intake unit aperture 922 towards a bottom area or floor of the chamber 700 or environment 3. The section 920 may be in fluidic communication with one or more extensions 924 extending along the bottom area or floor for collecting air, gas and/or particles therefrom. In some embodiments, the section 920 and/or extensions 924 may contain one or more intake apertures 412, 432 thereon.

The top 904 may include apertures 930 for the delivery of dry fog droplets 302 therefrom. The apertures 930 may be positioned proximal a fan 914 for encouraging circulation of the droplets 302 towards the top of the chamber 700 or enclosure 3.

Portions of the system 1 may be positioned outside the chamber 700 or enclosure 3. For example, a permanently installed or mobile collection system 400 may be positioned outside. In some embodiments, the fog generator 320 may be positioned outside the chamber 700 or enclosure 3 and disperse fog through apertures in the chamber 700 or enclosure 3. Sensors 160 may be positioned outside the chamber 700 or enclosure 3 for sensing the presence and/or quantity of gas or other actual conditions 22.

Safety Methods and Systems.

If it is determined that one or all of the mesh nebulizer modules are not working, the master controller 9, the dry fog control unit 360 or other control units described herein may flag an error. It may notify the operator through the user interface or the operator via text through the network communication system. The processor may control the piezo driver via an on/off signal. The processor may determine the condition of the nebulizer by reading the current sense signal via the analog to digital converter circuit.

Other components of the system 1 may include the network antenna for sending and receiving signals wirelessly, a light or other indicator tower for displaying indications, handles or other features for maneuvering the system or aspects thereof, and button for performing function such as locking/unlocking and starting/stopping.

In some embodiments, the system 1 and its control units may have one or more of the following modes of operation: idle mode 950, treatment mode 952 and hazard mode 954.

When in idle mode 950, the system 1 may be monitoring the sensors 160. The sensors 160 may be monitored in real time or may be monitored periodically. The control units may make determinations based on the actual conditions 22 sensed and select particular treatment profiles and their start times—a combination, for example, of solutions 10, ratio of solutions 10 and times for activation of the various subsystems 100, 200, 300, 400 and components thereof. These determinations may be sent to a server and/or interface for review and monitoring by a user. Any safety issues and/or threat levels 970 may be determined and so notified.

When in treatment mode 952, the system I may monitor the sensors 160 and make determinations to ensure components are working correctly, initiating cleaning procedures, adjusting treatment procedures, cancelling treatment procedures, and/or notifies the server and/or interface of any safety issues and/or threat levels 970.

When in hazard mode 954, the system 1 may display a threat level 970 notification and indication the emergency procedures related thereto. The system 1 may initiate the emergency procedures and send notifications to the server and/or interface.

According to some embodiments, the system 1 may include one or more of the following threat levels 970: a minor failure 972, a major failure 974, a minor hazard 976 and a major hazard 978.

Determination of a minor failure 972 may include failure of the dry fog system 300 that still permits shut-off of the generator 320 and/or nebulizing modules 386. A minor failure 972 does not require human intervention to prevent a hazardous condition. The system 1 may respond by shutting off the generator 320 and/or nebulizing modules 386 and initiating the collection system 400. A report notification may be sent to the server and/or user interface.

Determination of a major failure 974 may include wireless or electronic communication failure and/or failure within the collection system 400 that prevents collection and/or neutralization. A major failure 974 requires human intervention to prevent a hazardous condition. The system 1 may respond with alarm or user interface or server notifications that are self-generated as being unconnected to the wireless or electronic communication network. The system 1 may cease operation of the dry fog system 300 and may initiate the exhaust system 704.

Determination of a minor hazard 976 may include detecting gas outside of the chamber 700 or environment 3, the unsealing or opening of doors or apertures of the chamber 700 or environment 3, and/or clogged filters in the collection system 400. The system I may respond with a shutdown of the fog system 300 and activation of the collection system 400, as well as sending communications and/or alarms to the user interface or server.

Determination of a major hazard 978 may include a leak in the collection system 400 or exhaust system and/or failure by one or more sensors 160. Alarms and notifications may be sent by the system 1 for evacuate of personnel. Some shutdown procedures may include exhausting the air and gas from the chamber 700 or environment 3, instead of using the collection system 400.

The system 1 may be utilized to perform a leak test using a saline solution and saline sensors. The leak test may disperse the saline fog and collect the saline solution within the chamber 700 or environment 3 to ensure there are no leaks and that systems are operating safely.

General Features

The production system 100 and/or the preservation system 200 may be closed systems and may be in sealed engagement with each other. Further, the production system 100 and/or the preservation system 200 may be in sealed engagement with the dry fog production system 300.

Any of the tanks disclosed herein (e.g., 102, 106, 130, 140, 180, 190, 202, 234, 252, 260, 310, 336, 350, 380, 412) may be insulated, temperature-controlled and/or opaque using methods and systems described herein, or in the prior art. Any tanks may be comprised of or coated with any number of materials, including, but not limited to any combination or layered combination of glass, PVDF, Teflon (PTFE), Viton, Nitrile, Kalrez, or Acrylic. Any tanks may have a number of properties for blocking ultraviolet light or sunshine (e.g., including opaque, light reflecting materials), minimizing contact with environmental air, controlling the temperature and minimizing adverse interactions with any components or interior surface of the tank. Any tank may include water-tight and/or air-tight seals on their apertures to minimize interactions of their content with the environment 3. Whereas most tanks are closed within a system or sealed, some tanks, like the production tank 130, may include an open side for interacting with the environment 3. Some other tanks may permit gaseous exchange with the environment 3. Some tanks may include an insulating layer thereabout for further ensuring a stable or controllable internal temperature. Tanks may come in any number of shapes, and may be mobile or affixed with mobile features, such as wheels or handles. The tanks may include an aperture and/or valve on the nadir of the tank for easy emptying and/or cleaning.

The reservoirs 374 may be comprised of the same materials described above in relation to tanks. Alternatively, the reservoirs 374 may be comprised of, or contain a layer of, one or more of the following materials: plastic, rubber, HDPE, LDPE, EIHMWPE, PTFE, acrylic, polypropylene, Viton, PVDF, CPVC, Nitrile, EDPM, nitrile, neoprene, polyurethane, and silicone. The reservoirs 374, like tanks, may be resistant to certain chemical and/or contain gaskets or other designed components (e.g., check valves or membranes) to prevent leaks and form a watertight seal. Some designs may permit gaseous but not fluidic exchange.

Any of the valves disclosed herein 116, 174, 188 may include a combination of valves, tees, pumps, and/or couplings, and may be manually or automatically operated.

Any of the pumps disclosed herein 176, 186, 240, 242, 244, 338, 352, 406 may include a combination of pumps, valves and/or couplings, and may be manually or automatically operated.

The tanks may be interconnected using a plurality of hoses, valves and pumps to form closed systems. These interconnections may further involve apertures, regulators, sensors and/or controllers.

A hose may be any sealed, hollow mechanism capable of fluid flow therewithin (e.g., flexible hose or pipe or conduit).

Automatic operation may occur through one or more controllers known in the prior art and/or described herein. FIG. 23 depicts a communications infrastructure according to one embodiment. The system 1 may include a master controller 9 in wireless or electronic communication with any combination of controllers disclosed herein (e.g., 9, 220, 360, 440). Any of the controllers, which further includes the master controller 9 and controllers of the prior art, may include or being in communication with one or more sensors 160 for receiving sensed conditions. The controllers may include programmable logic circuits, memory and/or software to monitor and make determinations. Any of the controllers may be a standalone or web-based system. Each of the components of the system 1 may communicate electronically or wirelessly, amongst each other or through or in conjunction with one or more of the controllers. The controllers may be web-based and each system component may be in communication with the controller via wireless or wired internet connection(s). Internet connectivity may be facilitated by a Wi-Fi network with internet connectivity, an ethernet connection with internet connectivity or a wireless cellular data network connection. Additionally, the system architecture may not require a controller module or a relative humidity sensor, particle counter, chlorine gas sensor, or chlorine dioxide sensor if the timer-based system is implemented.

Any of the sensors 160 may be equipped to measure any number of conditions known in the prior art to be sensed (e.g., concentration, duration, temperature, pressure, flow rate, humidity, fill level, back flow, malfunctions, particle count, etc.). If any sensor or controller detects or determines a malfunction, an auto-shut-off and/or neutralization method may be initiated.

For each sensor or controller, a display panel, operational controls and/or wireless communication features for operation may be provided. The network communication system may be employ any signal transfer technology of the art, including Wi-Fi or cellular, as depicted in the top and bottom figures respectively below. The network communication system may, among enabling other functions, permit remote identification of machine issues for troubleshooting, generate field service work orders, collect and store information about the machine use.

The user interface of the machine may include an indicator tower, a screen, buttons and/or messaging communications. The user interface may indicate, display and/or provide control functionality. Machine modes, errors of the machine as a whole or components thereof, network connectivity, sensed or determined data, or status of the machine or components may be indicated or displayed. The network communication system may permit the user interface(s) to be housed on or proximal to the machine or sealed chamber, remotely positioned, and/or mobile.

The system I may permit a user to modify dry fog production, preservation, dispersal and/or collection characteristics or other critical parameters such as delivery period, delivery dosage, dwell period, fan speed, fan duty cycle, collection period, neutralization period, and/or ventilation/exhaust period.

What is claimed is:

1. A system for creating an artificial egg cuticle in a sealed environment, comprising:

a fog generator configured for dispersing a first solution as droplets sized less than ten microns, wherein the first solution includes two or more constituents;

a tower defining a vertical surface and a horizontal top opposite a horizontal base, the tower:

including a fan coupled with the horizontal top, further defining perforations along the vertical surface for receiving air therethrough when the fan is in operation, and wherein the perforations positioned proximal the horizontal base are larger than the perforations positioned distal the horizontal base.

2. The system of claim 1, wherein the two or more of the constituents include proteins and/or enzymes.

3. The system of claim 1:

wherein each of the two or more constituents is stored in corresponding reservoirs;

each of the one or more reservoirs is in fluidic communication with a mixing tank;

the mixing tank is in fluidic communication with the fog generator for providing the first solution to the fog generator for dispersal.

4. The system of claim 1, further comprising:

a second solution;

wherein the first solution is stored in a first reservoir and the second solution is stored in a second reservoir;

wherein each of the reservoirs are in fluidic communication with the fog generator;

a controller in communication with the fog generator for dispersing each of the solutions separately.

5. The system of claim 4, wherein the first solution is a cleaning solution and the second solution is an artificial cuticle including proteins and/or enzymes.

6. The system of claim 1, further comprising:

a second solution;

wherein the first solution is stored in a first reservoir in fluidic communication with the fog generator;

wherein the second solution is stored in a second reservoir in fluidic communication with a second fog generator;

a controller in communication with the fog generators for dispersing each of the solutions separately.

7. The system of claim 6, wherein the first solution is a cleaning solution and the second solution is an artificial cuticle including proteins and/or enzymes.

8. The system of claim 1, further comprising a structure including wheels for translation of the base, wherein the base supports thereon the fog generator and vertical tower.

9. The system of claim 1, further comprising:

a preservation tank having an exterior for blocking ultraviolet light, wherein the preservation tank is configured to store the first solution therewithin and is in fluidic communication with the fog generator;

a preservation pump for pumping the first solution from the preservation tank to the fog generator.

10. The system of claim 1, further comprising:

a humidity sensor configured to measure a relative humidity of the environment;

a water tank housing water and in fluidic communication with the fog generator;

a water pump in communication with the humidity sensor and configured for pumping the water to the fog generator for dispersal when the humidity sensor measures the relative humidity below a threshold relative humidity.

11. The system of claim 10, wherein the threshold relative humidity is 80%.

12. The system of claim 1, further comprising:

a humidity sensor configured to measure a relative humidity of the environment;

a water tank housing water and in fluidic communication with a humidifier;

a water pump in communication with the humidity sensor and configured for pumping the water to the humidifier for dispersal when the humidity sensor measures the relative humidity below a threshold relative humidity.

13. The system of claim 12, wherein the threshold relative humidity is 80%.

14. The system of claim 1, further comprising:

an air intake positioned within the sealed environment;

an air pump in fluidic communication with the air intake for pumping air from the environment through an air exhaust;

an air filter positioned within the air exhaust for filtering particles from the air.

* * * * *